(12) United States Patent
Matos

(10) Patent No.: US 10,607,730 B2
(45) Date of Patent: Mar. 31, 2020

(54) APPARATUS FOR PREVENTING UNAUTHORIZED ACCESS TO COMPUTER FILES AND FOR SECURING MEDICAL RECORDS

(71) Applicant: Jeffrey A. Matos, New Rochelle, NY (US)

(72) Inventor: Jeffrey A. Matos, New Rochelle, NY (US)

( * ) Notice: Subject to any disclaimer, the term of this patent is extended or adjusted under 35 U.S.C. 154(b) by 0 days.

(21) Appl. No.: 16/021,389

(22) Filed: Jun. 28, 2018

(65) Prior Publication Data

US 2018/0315493 A1 Nov. 1, 2018

Related U.S. Application Data

(60) Division of application No. 13/834,634, filed on Mar. 15, 2013, now Pat. No. 10,037,408, which is a continuation-in-part of application No. 13/563,399, filed on Jul. 31, 2012, now Pat. No. 9,152,837, which is a continuation-in-part of application No. 12/157,469, filed on Jun. 11, 2008, now Pat. No. 8,233,672.

(60) Provisional application No. 60/934,043, filed on Jun. 11, 2007.

(51) Int. Cl.
| | |
|---|---|
| *G06F 21/32* | (2013.01) |
| *G06K 9/00* | (2006.01) |
| *G07C 1/10* | (2006.01) |
| *G16H 10/60* | (2018.01) |
| *G06F 19/00* | (2018.01) |
| *G16H 80/00* | (2018.01) |

(52) U.S. Cl.
CPC ............ *G16H 10/60* (2018.01); *G06F 19/00* (2013.01); *G06F 21/32* (2013.01); *G16H 80/00* (2018.01)

(58) Field of Classification Search
CPC ........ G06F 19/00; G16H 10/60; G16H 40/63; G16H 50/20
USPC .......................................................... 705/3
See application file for complete search history.

(56) References Cited

U.S. PATENT DOCUMENTS

| | | | |
|---|---|---|---|
| 7,784,684 B2 | 8/2010 | Labrou et al. | |
| 2005/0149364 A1 | 7/2005 | Ombrellaro | |
| 2007/0258626 A1* | 11/2007 | Reiner | A61B 5/1171 |
| | | | 382/115 |
| 2013/0262155 A1 | 10/2013 | Hinkamp | |

* cited by examiner

*Primary Examiner* — Hiep V Nguyen
(74) *Attorney, Agent, or Firm* — Robert W. Morris; Ojeiku Aisiku; Eckert Seamans Cherin & Mellott LLC

(57) ABSTRACT

Apparatus and method for identifying and managing a requesting person who wishes to access information in a computer memory, calls for capturing local images of the requesting person and determining whether this person is the same as one of the registered persons whose identifying information is stored in a database. Identifying information stored in the database pertains to at least one visually observable biologic identifier on a body portion of each registered person. The accuracy of requesting person identification enhanced by allowing the access grantor of information to provide visual content which modulates the appearance of the biologic identifier of the requesting person. An identified human gatekeeper further hardens the system against inappropriate access. Utilization of the system for the documentation of encounters such as medical and other events is provided.

34 Claims, 41 Drawing Sheets

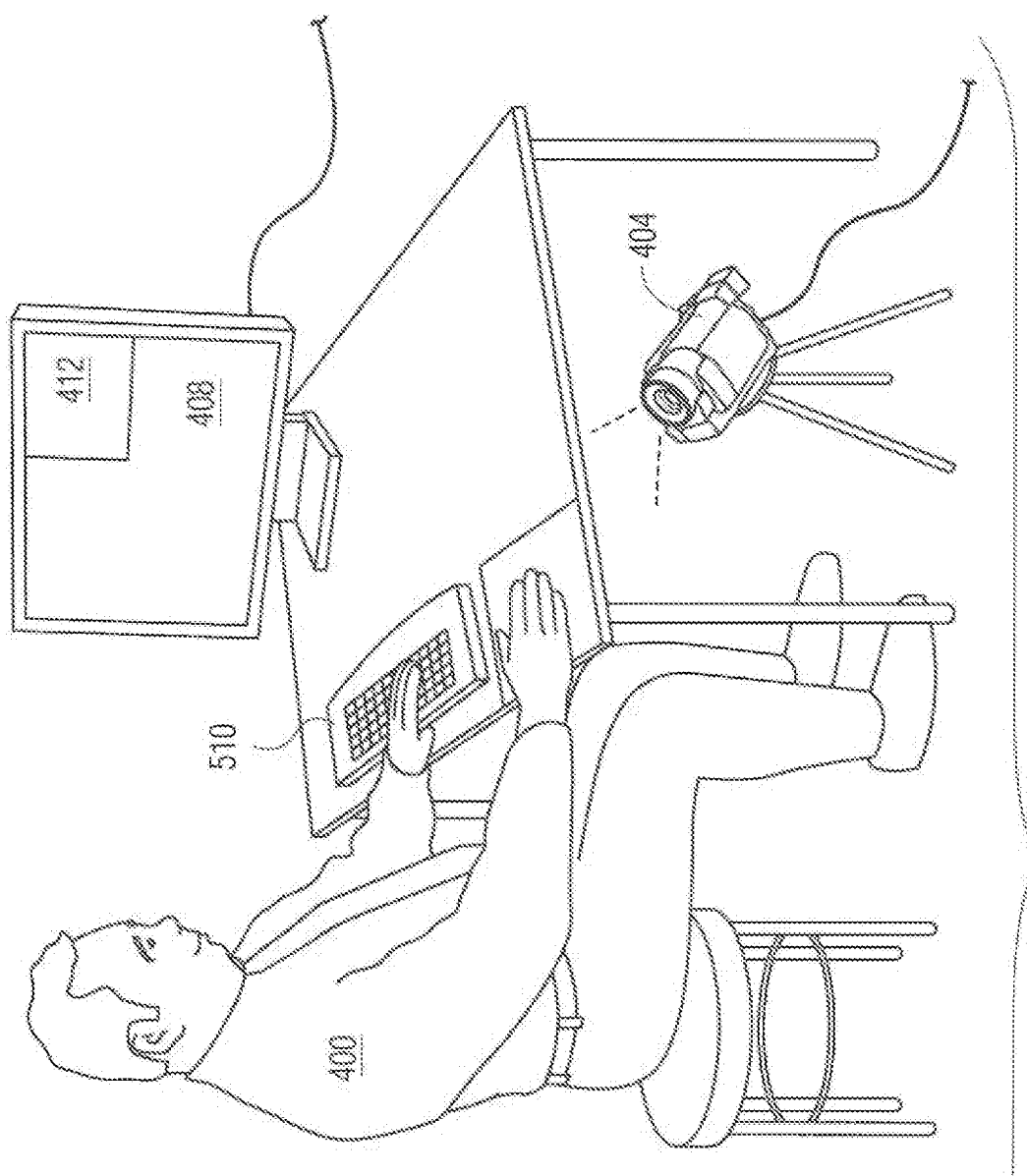
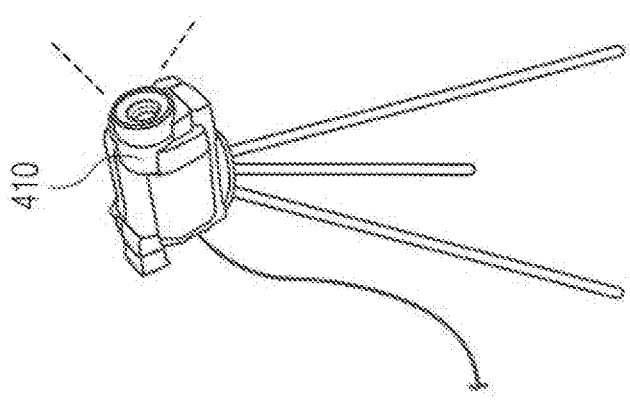
FIG. 5

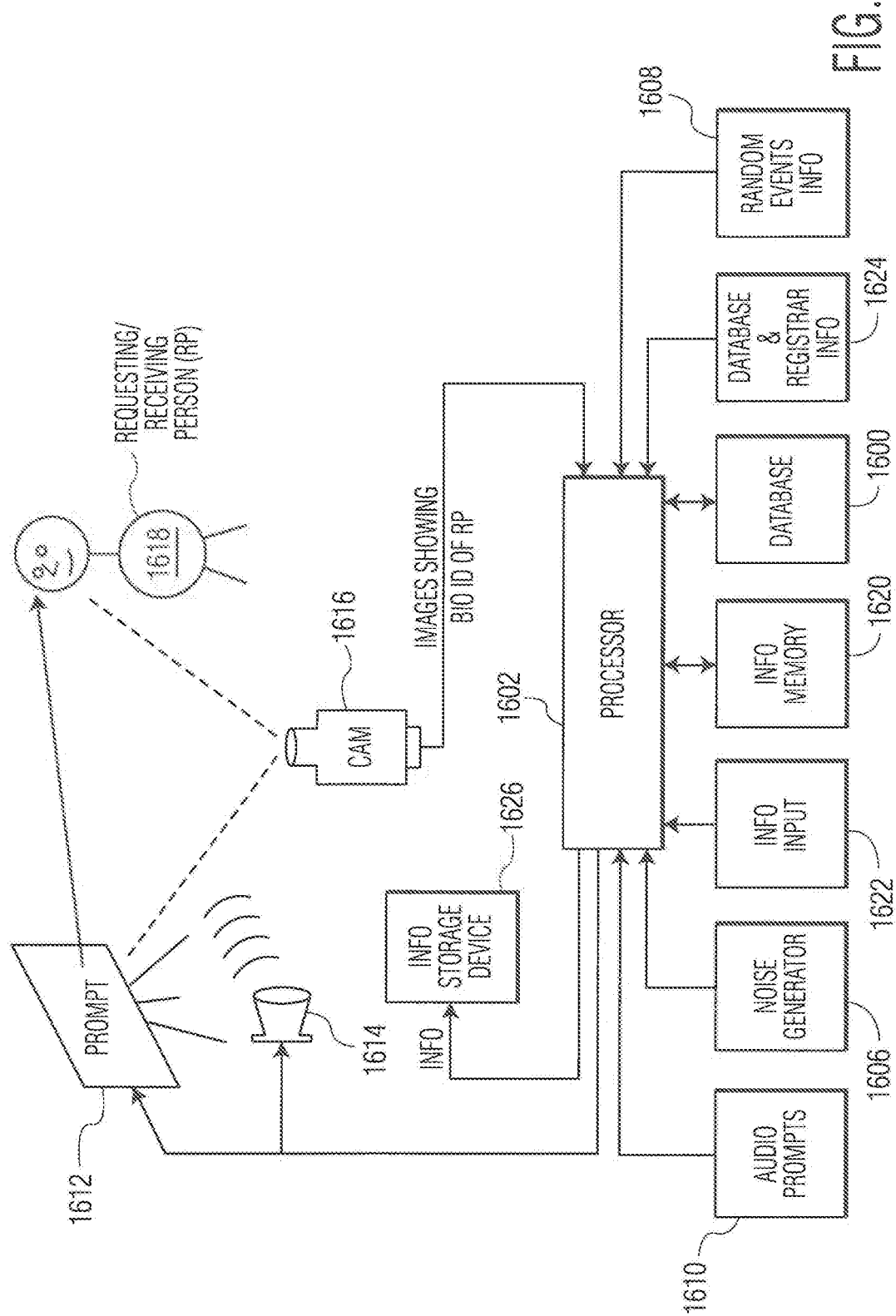

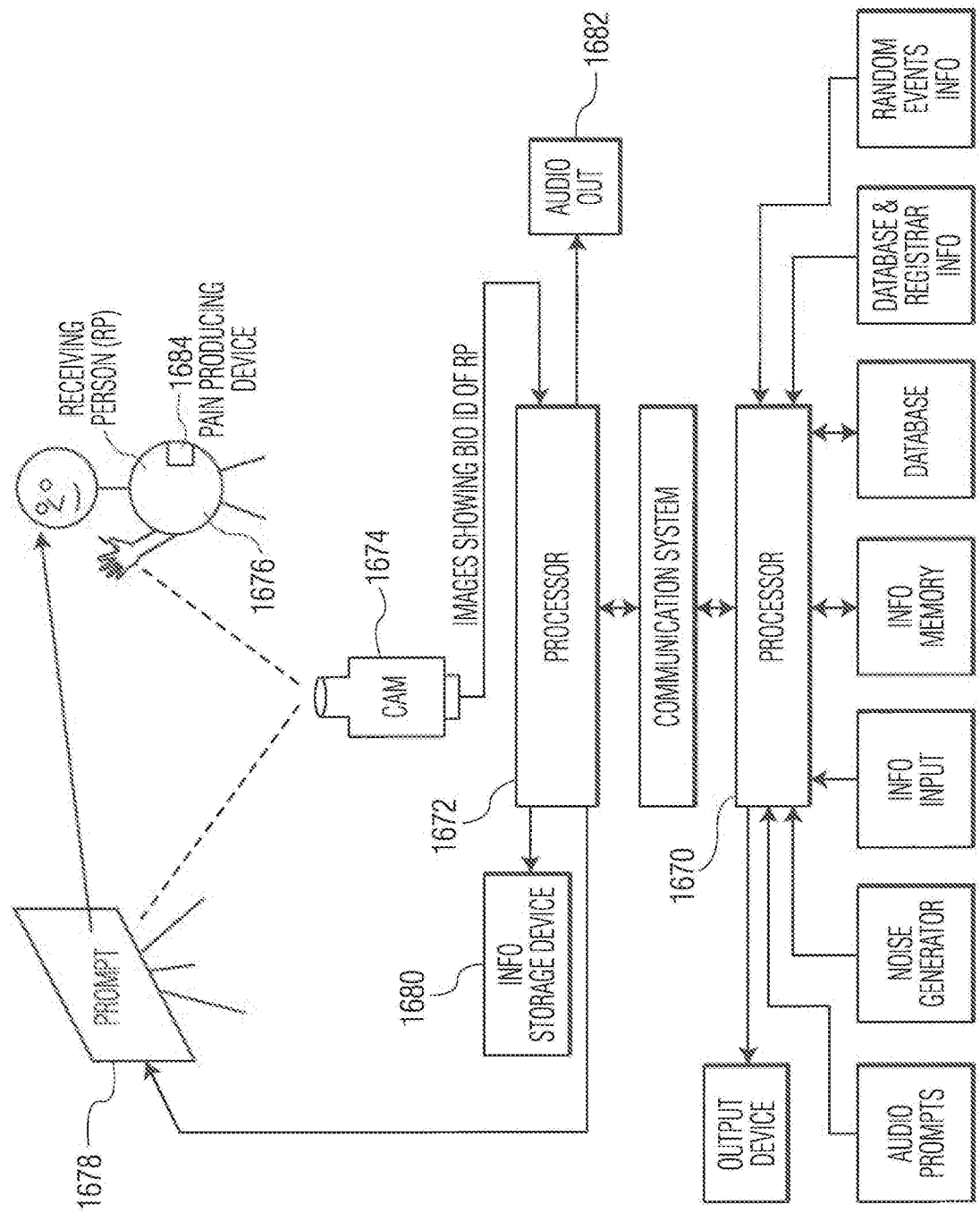

APPARATUS FOR PREVENTING UNAUTHORIZED ACCESS TO COMPUTER FILES AND FOR SECURING MEDICAL RECORDS

CROSS-REFERENCE TO RELATED APPLICATION

This present application claims the benefit of priority from U.S. Provisional Application Ser. No. 60/934,043, filed Jun. 11, 2007, entitled "APPARATUS AND METHODS FOR REMOTE VOTING AND FOR GOVERNMENT AND CORPORATE SYSTEMS BASED ON REMOTE VOTING," and claims the benefit of priority of the U.S. patent application Ser. No. 12/157,469, filed Jun. 11, 2008 (now U.S. Pat. No. 8,233,672) entitled "APPARATUS AND METHOD FOR VERIFYING THE IDENTITY OF AN AUTHOR" and claims the benefit of priority of the U.S. patent application Ser. No. 13/563,399 filed Jul. 31, 2012 (now U.S. Pat. No. 9,152,837) entitled "APPARATUS AND METHOD FOR VERIFYING THE IDENTITY OF AN AUTHOR AND A PERSON RECEIVING INFORMATION" (now U.S. Pat. No. 9,152,837) and claims the benefit of U.S. patent application Ser. No. 13/834,634, filed Mar. 15, 2013, entitled "APPARATUS FOR PREVENTING UNAUTHORIZED ACCESS TO COMPUTER FILES AND FOR SECURING MFDICAL RECORDS". The present application is a division of this latter, parent application.

The subject matter of the present application also relates to that of U.S. Pat. Nos. 7,835,824 and 7,991,517, both of which are incorporated herein by reference.

BACKGROUND OF THE INVENTION

There are a multitude of situations in which it is necessary to be able to document the identity of an individual who produces visually observable material or actions indicating the thoughts or decisions of that individual. Examples of such situations involve an individual who (i) produces written text material, (ii) indicates choices on a touch sensitive screen, (iii) produces alphanumeric entries using a keyboard, (iv) produces artwork, (v) produces a musical work with written material.

In addition, there are multiple situations where the determination and documentation of a person who desires to receive computer information, or to have access to a computer memory is vital. The incidence of computer hacking is increasing, and major breaches of a variety of types of assumed-to-be-secure systems has occurred. The invention described herein addresses this need by providing a means of identifying a person requesting information with a high degree of certainty.

The systems which perform such identification may be entirely processor-based, or may rely on the combination of processor and human abilities. Such combinations are a subject of the current invention.

The use of such highly secure systems for the storage and retrieval of critical information in which the participants are reliably identified allows for a secure system of medical records. Such an encounter identification system may be utilized for legal, business, and other transactions.

SUMMARY OF THE INVENTION

It is a principal object of the present invention to provide a method and apparatus which links the image of an individual (containing identifying features), obtained during a registration process, to the image of an individual author, during his or her act of generating the observable material that reflects the author's thoughts or decisions, thereby to verify the identity of the author with a high degree of confidence.

This object, as well as further objects which will become apparent from the discussion that follows, is achieved, in accordance with the invention, by apparatus which comprises:

(a) a computer database in which are stored an image of a visible identifying feature and other identification data of each of a plurality of registered human individuals;

(b) a computer processor coupled to the database for storing information therein and for accessing selected information therefrom; and (c) one or more input devices, coupled to the processor and disposed at a local site where an individual is to create writings or make computer entries. The input device(s) includes at least one camera arranged to view and capture a local image of both the identifying feature and at least a portion of a hand of the individual that is engaged in a writing or computer entry process.

The processor is operative to store the local image(s) in said database for later retrieval, and to compare the stored identifying feature of said registered human individuals with the local image(s) of the individual's identifying feature generated during the writing or computer entry process.

By such comparison, the apparatus can thus verify that the identity of the individual who made the writing or computer entry is the same as one of the registered individuals.

Similarly, the aforementioned objects of the present invention are achieved by a method for identifying the writer of a document which comprises the steps of:

(a) storing in a database identifying information for each of a plurality of registered human individuals, this identifying information including both an alphanumeric identifier and an image of a unique, visually observable biologic identifier on a body portion of the respective individual;

(b) capturing local images which include both:
  (i) making of at least one of writings and keyboard entries by an individual whose identifying information may be stored in the database; and
  (ii) a body portion of said one individual on which is visible said biologic identifier; and (c) determining whether said individual making the writings and/or keyboard entries is the same as one of the registered individuals whose identifying information is stored in said database, by verifying the substantial equivalence of the local image of the visually observable biological identifier and one said images of the body portion stored in the database.

Techniques for the identification of the receiver of information, the subject of U.S. Ser. No. 13/563,399, are complementary to the aforementioned techniques for author identification.

Such techniques utilize what is referred to herein as biodynamic identification, i.e. the use of a device in the vicinity of a person to be identified based on a visible or audible biologic feature, wherein the device causes a modification of the biologic identifier. For example, though a fingerprint provides a static identification, with a pattern that is unchanging during an encounter, the pattern of an iris of an eye will change based on constriction or dilation of the associated pupil in response to changing light conditions. Thus comparing a plurality of iris images obtained during a plurality of light conditions will enhance the biologic information available for identification. Furthermore, the identity of the receiver of information may be even more securely determined by allowing the sender of information to cause the manipulations which result in the change of the biologic identifier. For example, if the sender of information can repeatedly or continuously manipulate the amount of light impinging on the eye of a potential receiver of information, and can do so with a pattern of manipulations known only to the sender of information, then an analysis of iris images of the potential receiver of information by the potential sender of secure information will allow better identification of the receiving person than a simple static comparison (of a single iris pattern with data stored in the sender's computer memory).

Another technique of biodynamic identification is the provision of a display screen containing a detailed changing pattern in proximity to a biologic identifier of a receiving person. The screen may display white noise, other visual displays of noise, or other coded information. The content of the display is determined by the sender of the secure information. A composite image of (i) the potential receiver with biologic identifier (i.e. a face, an iris, etc.), and (ii) the displayed, changing coded pattern, when returned to the potential information sender will serve to indicate to the sender who the receiver A device which documents the parties to an encounter and the details of the encounter and which securely stores such encounter information is obtained by combining, with other apparatus and concepts, the use of:
  (1) the author identification apparatus and techniques presented in U.S. Pat. No. 8,233,672, incorporated herein by reference, and
  (2) the identification apparatus and techniques for a receiver of information presented in Ser. No. 13/563, 399, also incorporated herein by reference.

Such encounter identification ("EID") apparatus might, for example, provide a basis for a medical records system, wherein the parties to the encounter might be (i) a medical professional such as a physician, nurse, nurse practitioner, physicians assistant, dentist, etc.; and (ii) a patient treated by one of the aforementioned medical professionals.

Medical records systems, in order to be useful must combine ease of information entry and security of data storage. Currently available medical record systems have limitations including:
  (i) time consuming aspects of data entry;
  (ii) failure to document critical conversations between patients and medical professionals; and
  (iii) failure to securely store information.

The system described hereinbelow addresses these limitations. By providing video and audio documentation of encounters between medical professionals and patients, both of (i) and (ii) above are addressed. By identifying medical professionals and patients using biologic identifiers during a medical encounter, using the techniques of the above-cited '672 patent, a document which demonstrates the details of a medical encounter with an extraordinary degree of certainty (as to participants and information exchanged) is obtained.

Furthermore by requiring the biodynamic identification of a person who later desires to utilize the information contained in this medical record, the problem of inappropriate use of the information is addressed.

In a preferred embodiment of the invention, a hierarchy of registration persons determine
  (i) who may access secure information,
  (ii) what information may be accessed, and
  (iii) who may determine the individuals who are allowed to grant such access.

To maintain and enhance the security of the system, means are presented for the determination of the identity of these registration and supra-registration individuals using the aforementioned techniques of biodynamic identification.

The invention allows for all of the conventional techniques of medical record keeping and annotation. Conversion of voice to text is also possible, using techniques known in the art. Annotation with keyboard entries by a medical professional during or after an encounter are possible using techniques known in the art. Computer files may be inserted into the record indicating the results of examinations and tests.

The techniques herein may also be used to fully or partially capture a surgical procedure, with biodynamic identification of the participants.

The techniques herein may also be used to capture medical consent discussions, which in turn will largely if not completely resolve the problem of malpractice lawsuits related to the allegation of failure to provide informed consent.

The techniques herein may be applied to other types of encounters which depend critically on proper documentation, including proper identification of the individuals involved in the encounter. Such events include but are not limited to:
  (i) the parties to a contract;
  (ii) the parties to a sale of property;
  (iii) the parties to a law enforcement encounter;
  (iv) the parties to critical government proceedings; and
  (v) the parties to critical international proceedings.

To further enhance the computer file protection afforded by the biodynamic receiver identification apparatus which is the subject of Ser. No. 13/563,399, the addition of apparatus which enables a human gatekeeper is the subject of another embodiment of the invention. In such apparatus, a the human gatekeeping person, "HGP", must authorize access to computer memory, in addition to the authorization provided by the biodynamic identification performed by computer processors. In a first embodiment, the processor presents the results of such an analysis to the HGP, and the HGP makes a yes/no decision allowing or preventing information access. In a second embodiment, a yes/allow access decision requires both a suitable identification match by the processor, and a permission by the HGP.

For a full understanding of the present invention, reference should now be made to the following detailed description of the preferred embodiments of the invention as illustrated in the accompanying drawings.

BRIEF DESCRIPTION OF THE DRAWINGS

FIG. 5 shows another representational diagram of an apparatus for registration and author data and image capture.

FIG. 16A is a block diagram of apparatus in a second preferred embodiment of the invention.

FIG. 16C is a yet another block diagram of apparatus in a second preferred embodiment of the invention.

DETAILED DESCRIPTION OF THE PREFERRED EMBODIMENTS

Figure 1:
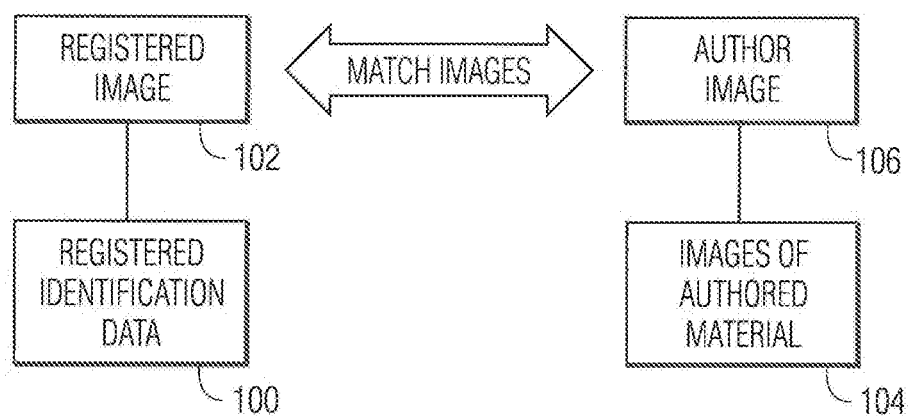
FIG. 1 is a block diagram which illustrates the basic concept underlying one aspect of the present invention.

The preferred embodiments of the invention will now be described with reference to FIGS. 1-32B of the drawings. Identical elements in the various Figures are identified by the same reference numerals.

FIG. 1 shows the conceptual basis of one of the inventions herein. In order to prove who the author of a document is (i.e. to prove the identity of an author of a document), the following three links are established:

1) At a registration event: a link between the name of the author (and/or other author identification data) 100 and a video image 102 that identifies the author;
2) At an authorship event (the time an author produces an original document): a simultaneously recorded image of
   a. the document as it is being authored 104, and
   b. an author image 106, i.e. an image of an identifiable feature of the author; and
3) At a verification event (a time when verification of the author identity is confirmed): a determination that the registered author image 102 is substantially identical to the author image 106 which is recorded at the time that the document is authored.

The registration event links 100 and 102; the authorship event links 106 and 104; and the verification event links 102 and 106. The net effect, symbolically is:

100←→102←→106←→104

. . . thereby establishing that the author is the same person as a registered person.

The document may be one of many types in which there needs to be certainty about the identity of the person who signed it, who authored it, or who indicated his or her thought(s) by one or more writings or keyboard entries. Examples include, but are not limited to:

a) a financial matter which requires a verified signature, such as a check, a loan application, a promissory note, a funds transfer, etc.;
b) a test, in which the test taker answers questions to demonstrate mastery of certain matters;
c) an original work—literary, scientific, artistic, musical, etc.

d) a vote—in a government election, a shareholder matter, etc.

e) a medical record—including an entry by a physician or nurse, a signature on a "do not resuscitate order"; a signature (by a patient or physician) on a document indicating that informed consent was obtained;

f) a legal document; such as a contract, a death certificate; a court document; a will; and g) a political document such as presidential signature on a legislative bill, a treaty, etc.

The term "author" is intended to include each of the types of person listed in a)-g) hereinabove; and in general is anyone whose identity is to be linked to an observable event. This identity may be a name, a social security number, a medical license number, etc. The observable event generally refers to events which may be seen; But embodiments of the invention which involve only video data, or only audio data (e.g. verification of a speaker or singer) are possible. The events which may be seen include writing using a pen, pencil etc. on a piece of paper, using a virtual pen to write on a touch sensitive screen, selecting a choice from a menu using a touch sensitive screen; using an actual keyboard, and using artistic tools to create a work of art.

Figure 2:
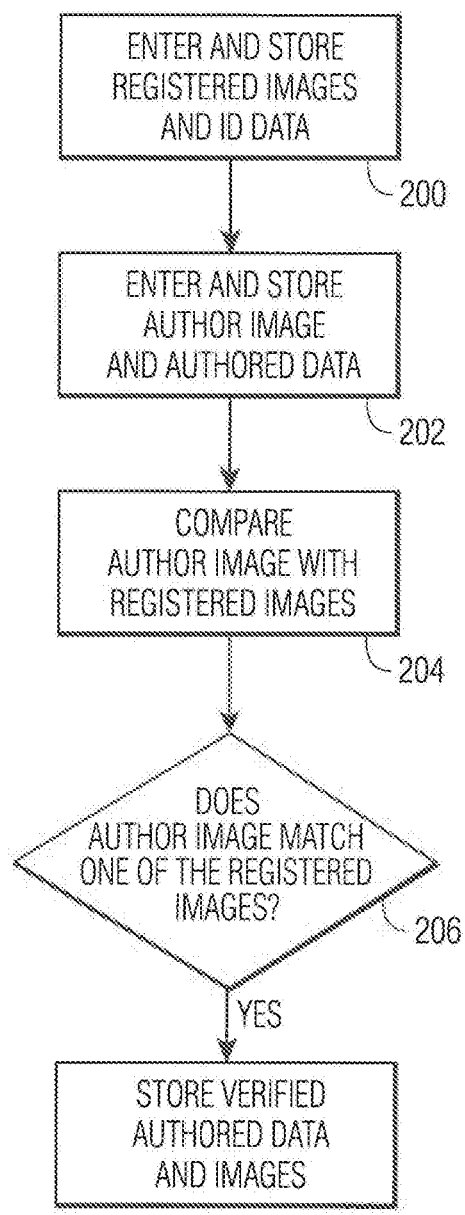
FIG. 2 shows a flow diagram of the steps followed in a first preferred embodiment of the invention.

FIG. 2 is a flow diagram which parallels the conceptual schematic of FIG. 1. It shows one possible sequence of events by which the 3 aforementioned linkages may occur which link the name of an author to the authored material. First, a registration process 200 ensues, in which a link is established between "ID data" i.e. a person's name or other identifier (e.g. social security number) and registered images, i.e. a unique visual image of that person (e.g. the face, one or more fingerprints, an iris pattern, a retinal blood vessel pattern, a palm print, signature, etc.). For the registration to occur, a person—the "registrar"—must indicate that they accept the link between the ID data and the person's image. The process may be similar to an appearance before a notary public, but it could be (i) simpler (e.g. self identification), more (ii) complex (e.g. requiring multiple witnesses, and/or requiring confirmation of one or more biologic identifiers (e.g. fingerprints) from a data bank of such biologic identifiers).

Once the registrar accepts the association between the ID data and the registering person's image, the data-image pair is stored as a computer file in a database. The image of the data-image pair is then considered to be a registered image. A database may hold:

a) one or multiple registered images of one person;

b) registered images of multiple persons (which may include one or more images for each such person).

At block 202, at a time later than the registration process, an author (as defined hereinabove) who has previously registered (by the process indicated hereinabove) and who wishes to have his (male pronoun used hereinbelow without any intention of the choice indicating a preference, limitation, or advantage) identity confirmed, produces a document while simultaneous images are obtained showing:

(i) the authored data, i.e. the actual writing as it is being produced, or (ii) keystrokes as they are being registered (on either an actual or virtual keyboard); and (ii) the author image, i.e. an identifiable biologic feature of the author.

In one preferred embodiment of the invention, the camera which captures the authored data also captures—within the same image—the author image. For example, the camera may be situated so as to capture both the face and the hands of the author, with the portion showing the hands also showing the written material/keystrokes in enough detail to identify its content. Ideally the camera would also show enough of the body region between the face and the hands, so that it was clear that the face and the hands belonged to the same person.

An example (discussed hereinbelow) which clearly demonstrates textual material and author identification in a single image, uses a device which shows author fingerprints, as the author makes keyboard entries.

In another preferred embodiment of the invention, two separate cameras may be used: one to capture the image of the biologic identifier, and one to capture the image of the textual material. The two images may stored as separate files with a secure label for each file, indicating the time and location of each image (to thereby allow for the conclusion that the two were recorded in essentially the same space and time); Alternatively, the two images may be merged into a single file, by techniques known in the art.

At block 204, the author image is compared with either (i) the registered image of the person believed to be the same person as the author; or (ii) some or all of the registered persons, if the identity of the author is either unknown, or substantially uncertain.

At block 206, a determination is made as to whether the author image and a registered image are a match. The definition of a match is further discussed hereinbelow in conjunction with FIG. 3. If a match is present, block 206 leads to block 208, and the authored data and images are labeled as verified, and stored as verified.

Figure 3:
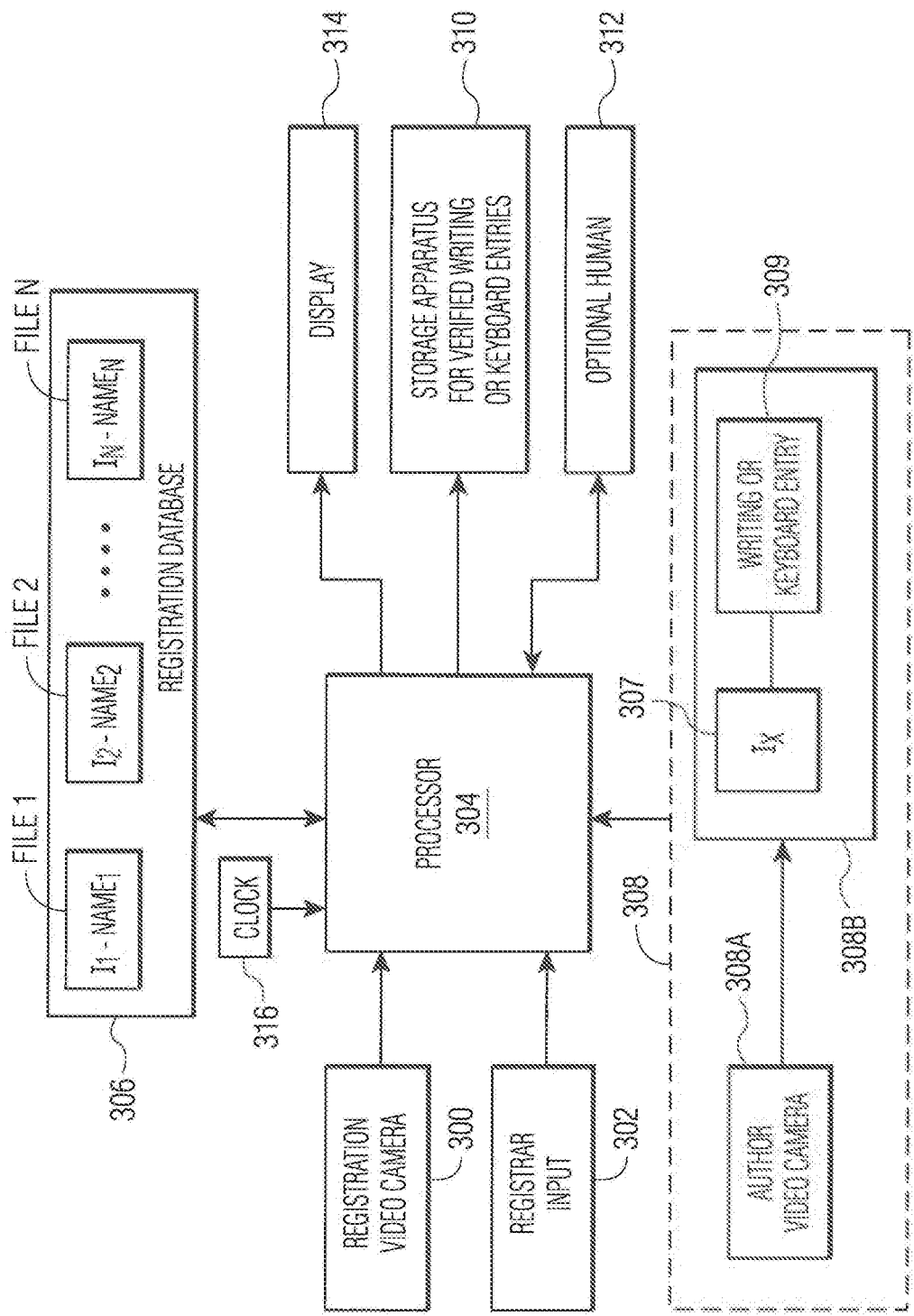
FIG. 3 shows a block diagram of the apparatus in said first preferred embodiment of the invention.

FIG. 3 shows an example of apparatus which performs the functions of the invention described herein.

Registration video camera 300 allows inputting of images of a biologic identifier such as a face, palm, fingerprint(s), iris or retinal image, to processor 304. A registrar confirms the name or other textual identifier (the ID data) to be associated with the image from 300, and enters the textual identifier through input 302, to processor 304. 304 produces a file which contains both the ID data and the associated video image, and stores the information as a file in registration database 306. 306 contains multiple files (e.g. FILE 1), each of which contains one person's ID data and that person's identifying image (e.g. $I_1$-$NAME_1$). 306 is preferably maintained in a highly secure environment. Various means to prevent corruption of the data contained in 306 are known in the art. Maintaining multiple copies of the database in different locations, and requiring a match with two or more copies, each in a different location is one means of enhancing the security of the database.

An author wishing to prove his identity, enters video images of (i) his work as it is being produced by him, and (ii) himself, through input device 308. Video camera 308A is used to produce file 308B, which contains simultaneously recorded author image(s) 307 and authored data image(s) 309. In an alternate embodiment of the invention, as discussed hereinabove and hereinbelow, there may be more than one camera 308A. 308B is sent to processor 304, which then compares the author image 307 with one or more registered images in database 306. If a match is found, the author data 309—i.e. the signature, composition, document, etc. produced by the author—is then stored as verified writing or keyboard entries in storage apparatus 310. Storage apparatus 310 may be part of 306, or separate from it.

The comparison of the author image and the registered image may be:

a) performed entirely by processor 304;

b) performed entirely by optional human 312, who views the two images on display 314;

c) performed by processor 304, unless the result of the evaluation by 304 results in a state of uncertainty (e.g. if there is a less than good match between the two images)—In this case, the task of comparison may be handed off to human 312. Processor 304 may be pre-programmed to indicate the level of goodness of match required to bypass human 312. Processor 304 may use neural networks to facilitate the process of visual comparison.

If the final decision regarding the comparison is made by the processor, the result may be indicated on display 314. Clock 316 allows for time-stamping of images and of comparisons.

The recording by any of the cameras—either during the registration step or the authoring step—may be of a single image or of a sequence of images (e.g. a video or a "movie"). Hereinabove and hereinbelow, "image" is intended to refer to either one of these cases.

Figure 4:
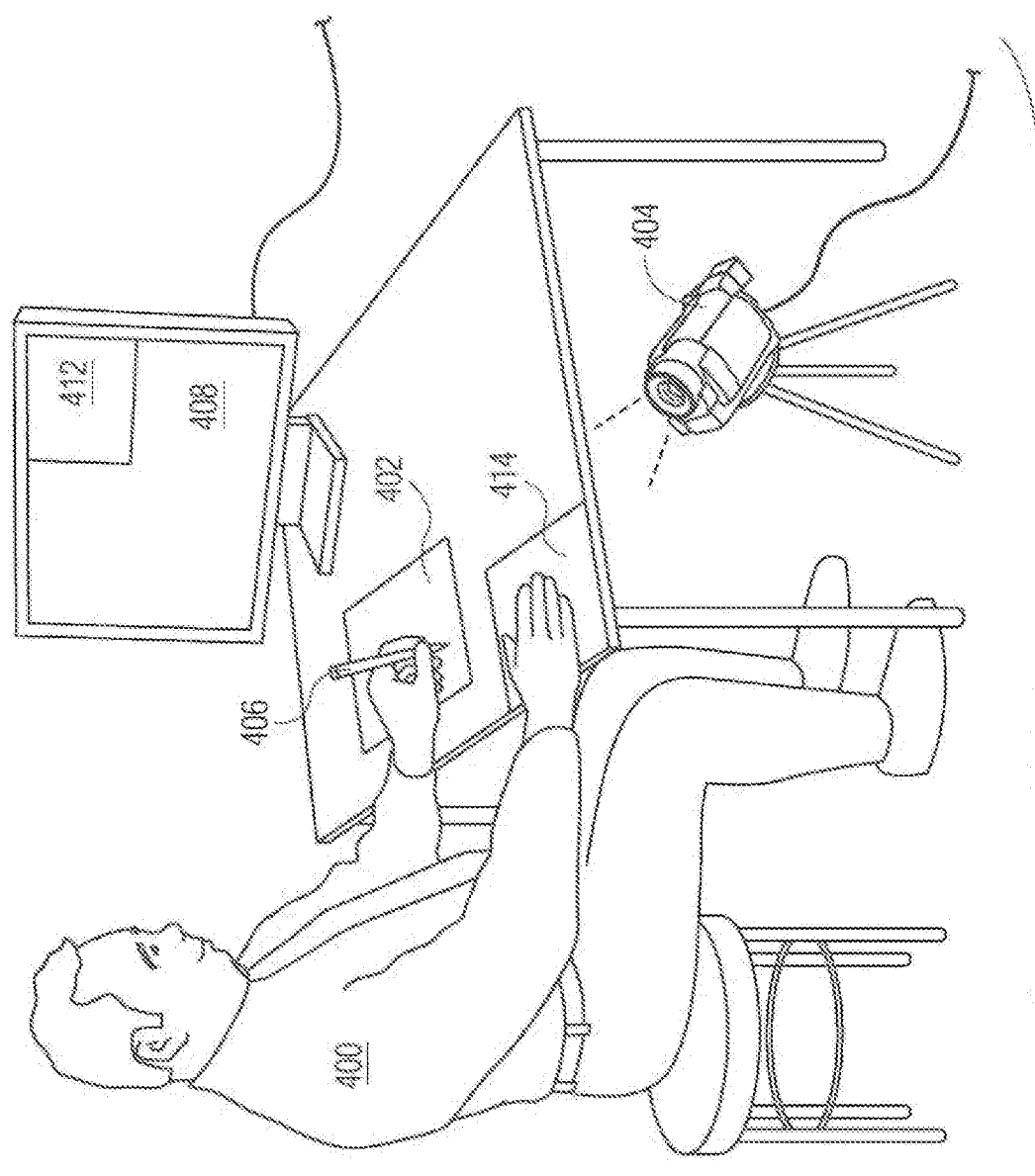
FIG. 4 shows a representational diagram of an apparatus for registration and author data and image capture.

FIG. 4 shows a person 400 using one embodiment of the apparatus shown schematically in FIG. 3. The apparatus shown in FIG. 4 may be used for:
  a) registration;
  b) entries by an author who wishes to be a verified author; or
  c) both a) and b).

In the registration process, person 400 may use the apparatus to input two or more unique identifiers simultaneously, in the same image. For example, 400 may sign his name on 402. 402 may represent:
  a) a transparent or semi-transparent surface/paper which allows a signature to be observed and recorded by video camera 404 which is situated below 402;
  b) a touch sensitive screen with enough resolution to provide a good quality copy of a signature. 404 may be used to capture both the signature and
  a) an image of the face, iris or retina of 400; and/or
  b) an image of one or more fingerprints, or a palm print of 400, visualized through transparent surface 414.

Alternatively, 404 may capture both a fingerprint/palm print and a signature, without capturing the facial/iris/retinal image.

In yet another embodiment of the apparatus used for registration, multiple identifiers may be simultaneously captured in the same image using camera 410 which is situated behind and, if necessary, somewhat to the side of (or above) person 400, and may be pointed at mirror 412. With proper placement of 410 and 412, and proper angulation of 412, camera 410 may visualize both:
  a) the signature of person 400 on 402 (which need not be transparent or semi-transparent in this case); and
  b) the face/iris/retina of person 400.

In yet another alternate embodiment of the registration apparatus, 410 and 404 may both be used to input registration information. Each may be used to input the type of information described hereinabove. The information may be stored:
  a) as two separate files, one for each camera, with each having associated ID data for the registrant, and each confirmed by the registrar (with each file preferably indicating the presence of additional registration information for the same person in another file); or
  b) as a single file.

The information from 404 and 410 may be obtained simultaneously or at separate times.

A simplified form of the registration process would be to enter only a single identifier for 400, e.g. one of the signature, facial image, etc. The apparatus in FIG. 4 could be used for this purpose. Cameras with other locations (e.g. facing 400, or above 400) are also possible. Scanning a signature or fingerprint into processor 304 (of FIG. 3), using a scanner, as is known in the art (and not shown in the Figure) is also possible.

Embodiments of the registration apparatus with more than two cameras are possible. The operating principles parallel those of the two-camera case.

The apparatus shown in FIG. 4 may also be used for the entry of the author image and authored data (202 in FIG. 2). In this case, the apparatus is used to simultaneously enter:
  a) written entries or touch sensitive screen based entries; and
  b) at least one visual identifier of the author (e.g. face, signature, fingerprint(s), etc.).

The mode of operation would be the similar to that described hereinabove for the registration process, except that it may be desirable to enter more text (perhaps a lot more text) than just the author's signature. Furthermore, screen 408 may be viewed by camera 410, and may be used to display either:
  (i) textual material in a document that the author is signing; or
  (ii) a display of what the author is writing on 402 (as observed by camera 404 or another camera (not shown in this Figure) which may be placed above 402). In addition, by angulating mirror 412 so that it shows the author's face, and by properly angulating 408 and 412 and properly positioning 410, both the face (and/or iris, and/or retina) and the authored data as shown on screen 408, may be recorded in a single image by 410 (or in each of a series of images recorded by 410).

FIG. 5 shows a version of the apparatus similar to that shown in FIG. 4, except that writing surface/touch sensitive screen 402 has been replaced by keyboard 510. All of the specification in conjunction with FIG. 4 is applicable to the apparatus shown in FIG. 5. If 510 is a conventional keyboard, then keyboard entries will not be seen from camera 404; They will be viewable from 410, with a proper geometric arrangement of 410, 408 and 412, as discussed hereinabove.

In an alternate embodiment of the invention, a largely transparent keyboard could be used for 510. This would facilitate 404 observing the face of 400.

Figure 6:
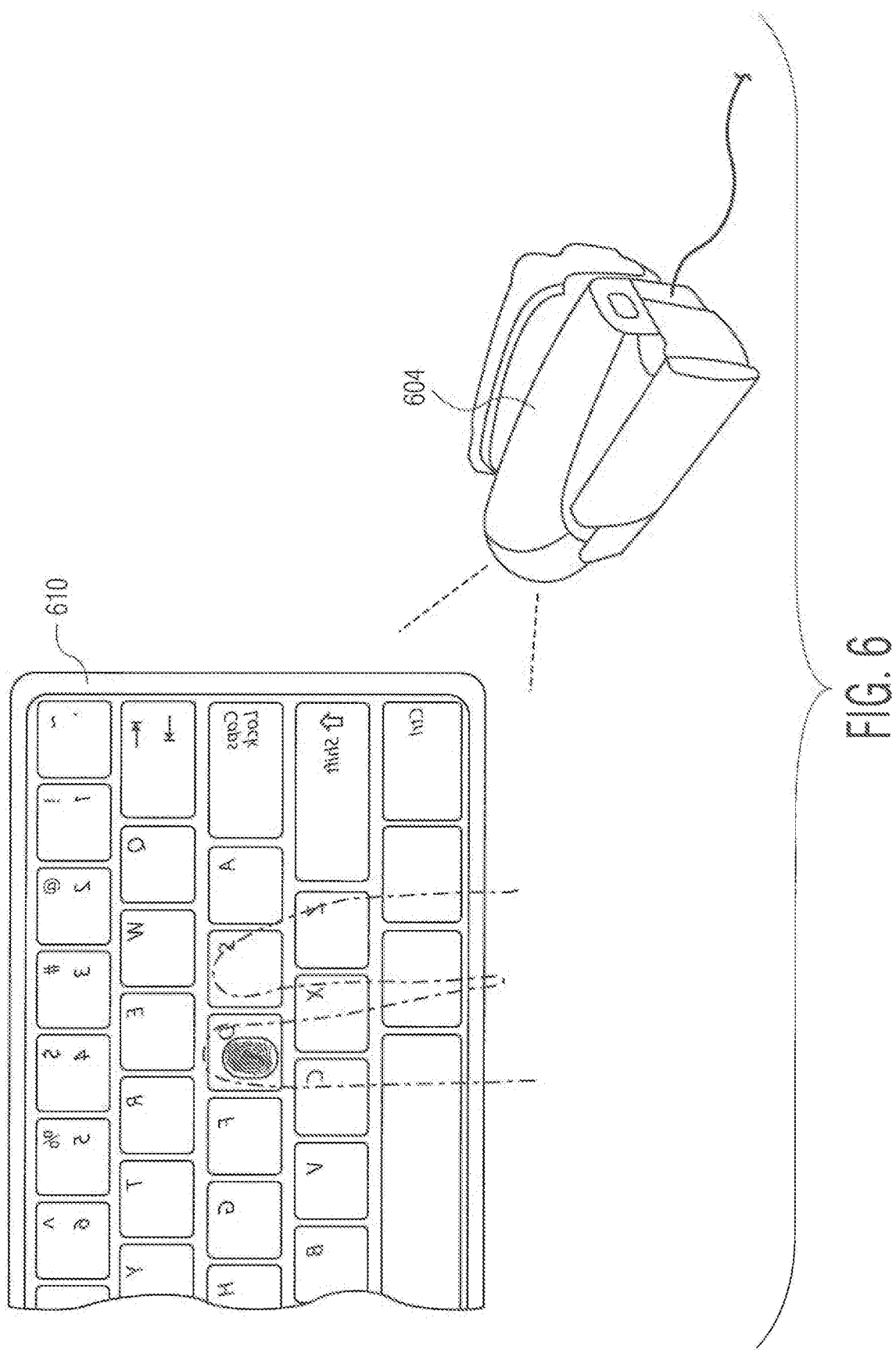
FIG. 6 shows a representational diagram of apparatus which allows for simultaneous viewing of a fingerprint and a keyboard entry.

Furthermore, a keyboard in which the key surfaces are largely transparent—shown in FIG. 6—would allow simultaneous observation of both:
  a) the author's fingerprint, and
  b) the sequence of selected keystrokes.

In the Figure, camera 604 is positioned underneath keyboard 610, to show both fingerprints and keystrokes in each image.

Figure 7:
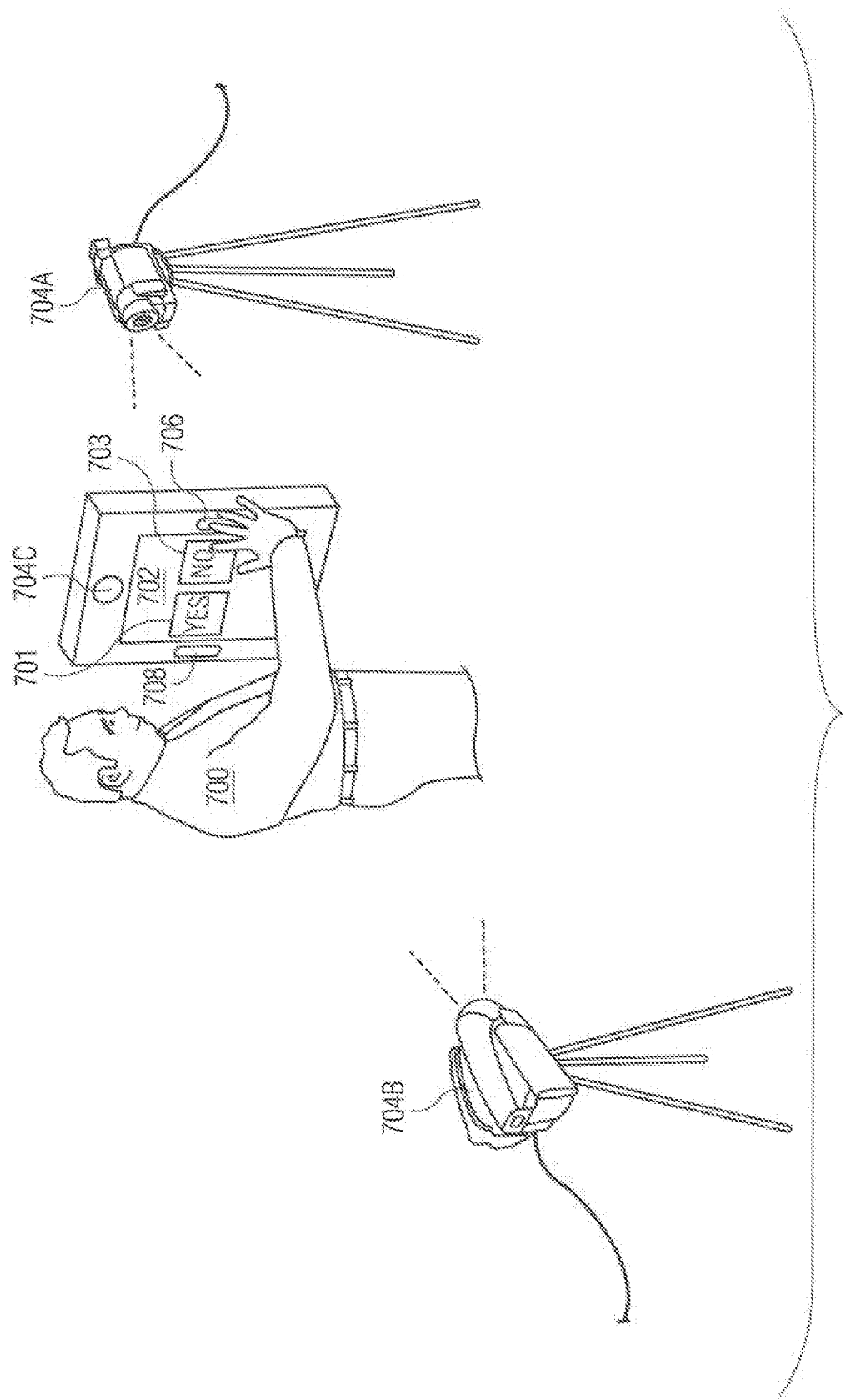
FIG. 7 shows a representational view of apparatus for simultaneously recording a fingerprint and a choice on a touch sensitive screen, containing three video cameras.

FIG. 7 shows another embodiment of the invention which allows for the simultaneous viewing by a single camera of (i) a biologic identifier of an individual making a choice, and (ii) the choice. In this case, the choice is indicated by the individual by his selection on a touch sensitive screen 702. In the Figure person 700 has the option of indicating either a "yes" or a "no" choice. As shown in the Figure, he may indicate "no" by touching touch sensitive box 703. As he does so, he simultaneously touches fingerprint identification apparatus 706 with another finger. The documentation that the fingerprint recorded by 706 comes from the same individual as the "no" choice may be accomplished by:
  a) a camera 704A located behind the transparent or semitransparent touch sensitive screen which records an image which shows each of (i) the finger touching the "no" choice box, 703, (ii) the contiguous parts of the hand lying between the finger which selects the touch sensitive region and the finger which is the source of the print, and, optionally (iii) the fingerprint itself, viewable through 706; and b) a camera 704B which is located behind the individual, and records the selection of the "no" choice at the same moment that the fingerprint is visualized by 706.

In the case of a "yes" choice, the functioning of the apparatus is analogous to its functioning for a "no" choice: The left hand of 700 may be used to simultaneously touch fingerprint identification apparatus 708 and touch box 701 on the touch sensitive screen.

Apparatus similar to that shown in FIG. 7 with two choices other than "yes" or "no" will function in an analogous manner to that described hereinabove. Apparatus with more than two choices will also function in an analogous manner. For example, the right side of screen 200 may contain two or more touch sensitive virtual buttons, each associated with an adjacent fingerprint scanner. In an alternative embodiment of the invention, the hand which is the source of the fingerprint need not be the source of the choice selected on the touch sensitive screen. What is required is that there be visual evidence that the individual who makes the touch sensitive screen selection is the same individual as the one who is the source of the fingerprint; This may be accomplished by camera 704A alone, or by 704A in conjunction with either (i) 704B, (ii) camera 704C, which faces the individual, or (iii) 704B and 704C together.

Figure 8:
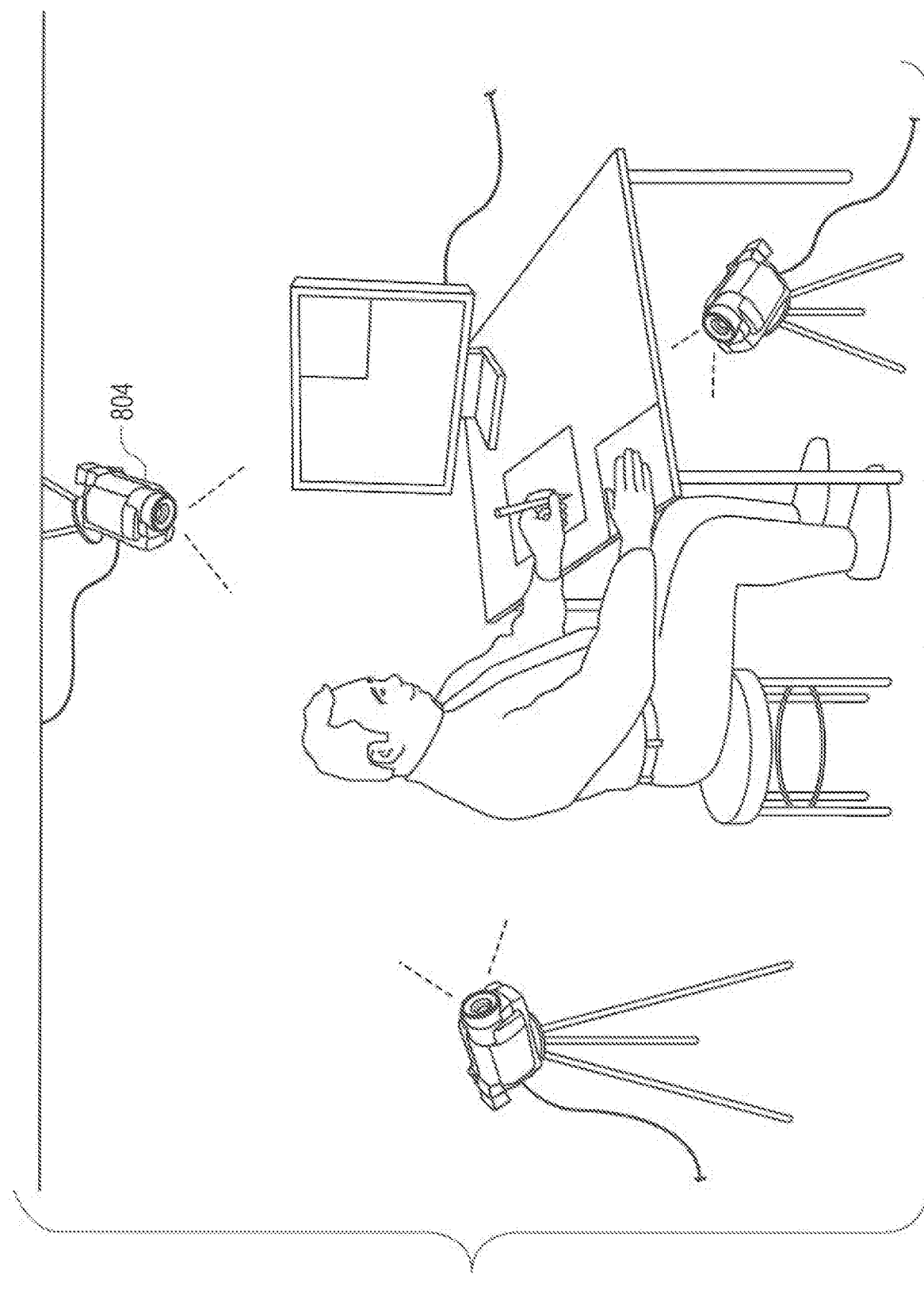
FIG. 8 shows a representational diagram of an apparatus for registration and author data and image capture, with an overhead camera.

FIG. 8 shows an example of apparatus similar to that of FIG. 4, with the addition of ceiling mounted camera 804. The purpose of the overhead camera is to simultaneously visualize both the face of the author of the writing and the writing itself. The camera need not be ceiling mounted, and could be in a variety of locations. The individual need not be writing, and could be using either a keyboard or a touch sensitive screen.

Figure 9:
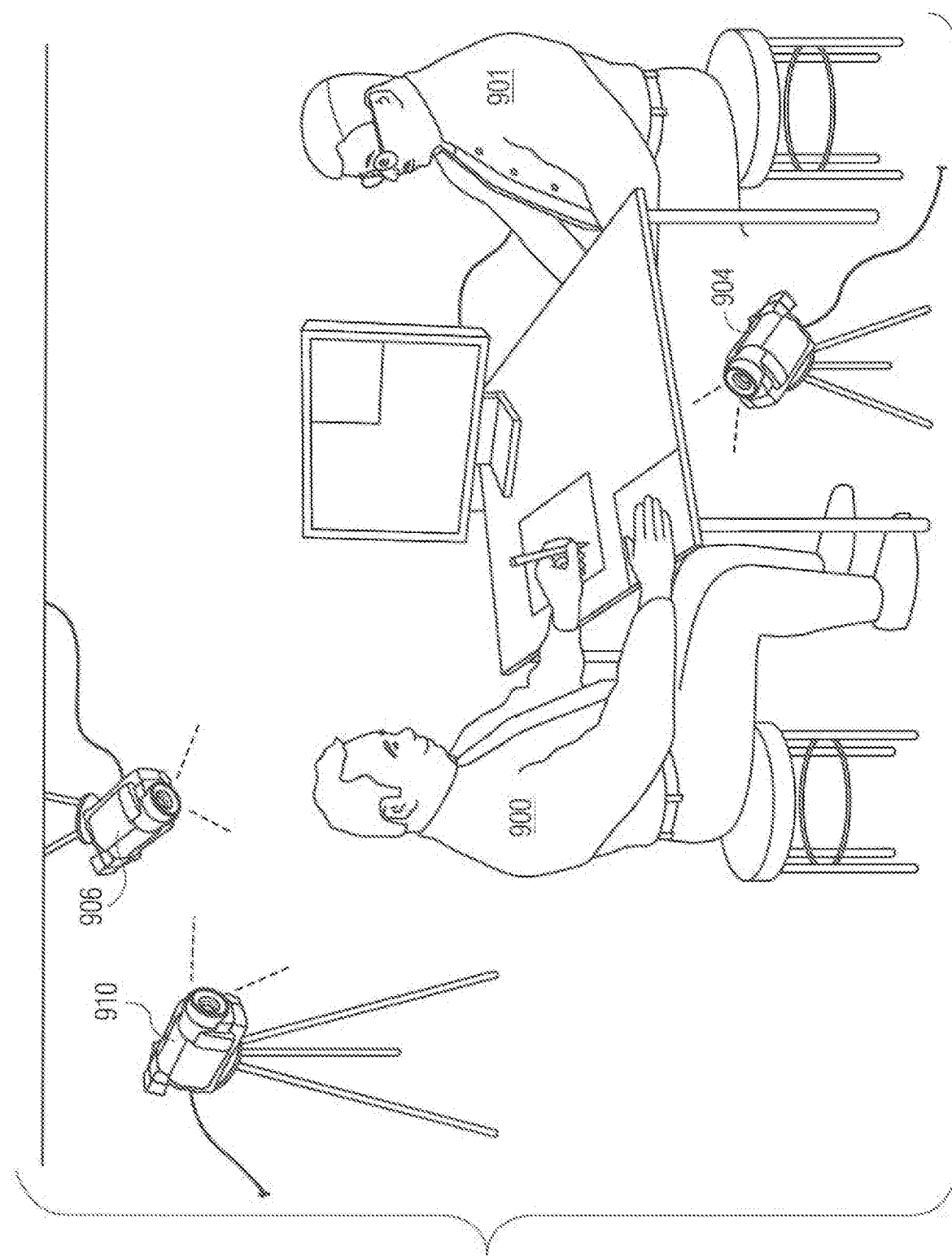
FIG. 9 shows a representational diagram of an apparatus for registration and author data and image capture, with an overhead camera and a witness to the process, whose image is also to be captured.

FIG. 9 shows the same apparatus as that of FIG. 4 with the addition of a witness 901. In one version, the witness functions as a conventional witness, i.e. he may sign a document indicating that he witnessed the writing by person 900. In another version, he may, exchange places with 900, after 900 completes his writing, and the same process (as is described in the specification hereinabove in conjunction with the apparatus shown in FIG. 4) which records one or more images of 900 may then record one or more images of 901 as he signs indicating his witnessing. In conjunction with the aforementioned two versions, the functioning of camera 904 is analogous to that of 404 in FIG. 4, and the functioning of camera 910 is analogous to that of 410 in FIG. 4. Preferably person 901 is a person who has previously undergone the registration process described hereinabove, so that his being an identifiable witness is established. In a preferred embodiment, an identifying image of the witness is captured within the same camera image as at least one of (i) an identifying image of the writing person 900, and (ii) the written material. A variety of camera locations and orientations, and, if desired, mirror location(s) and orientations may be used to accomplish this task; Cameras 906 and 910 illustrate two possible camera locations for this task.

Figure 10:
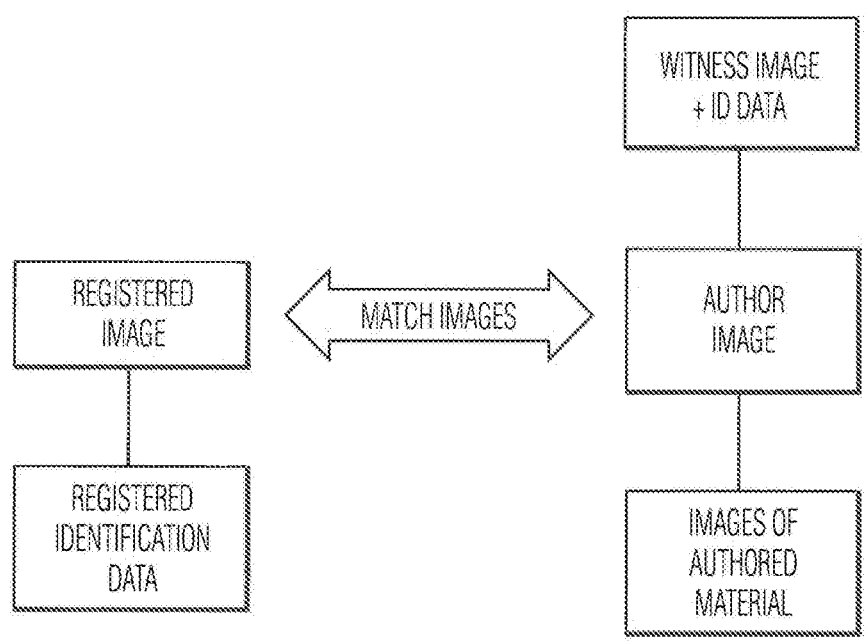
FIG. 10 shows a schematic diagram which illustrates the concept underlying the invention when the image of a witness is captured at the time of the authoring step.

FIG. 10 shows a conceptual schematic, analogous to FIG. 1, which indicates the role of the witness in enhancing the robustness of the identification system. By including within one image:

(i) the authored material;
(ii) the author image; and
(iii) the witness image;

a highly verifiable and very difficult to corrupt/hack, system is the result. If in addition (not shown in the Figure), the witness is also a person who has been registered by the same process that the author has, an even greater degree of hardening of the system is the result.

Since the registrar has the role of matching the ID data and the registered images, the robustness of the system will depend on the reliability of the registrar. Various methods of enhancing registrar reliability are possible including having multiple registrars, each of whom reviews the correctness of a paired ID data-registration image set. Yet another method of security enhancement would be to have super-registrars, i.e. people with a high level of security clearance who are responsible for registering ordinary registrars.

Figure 11:
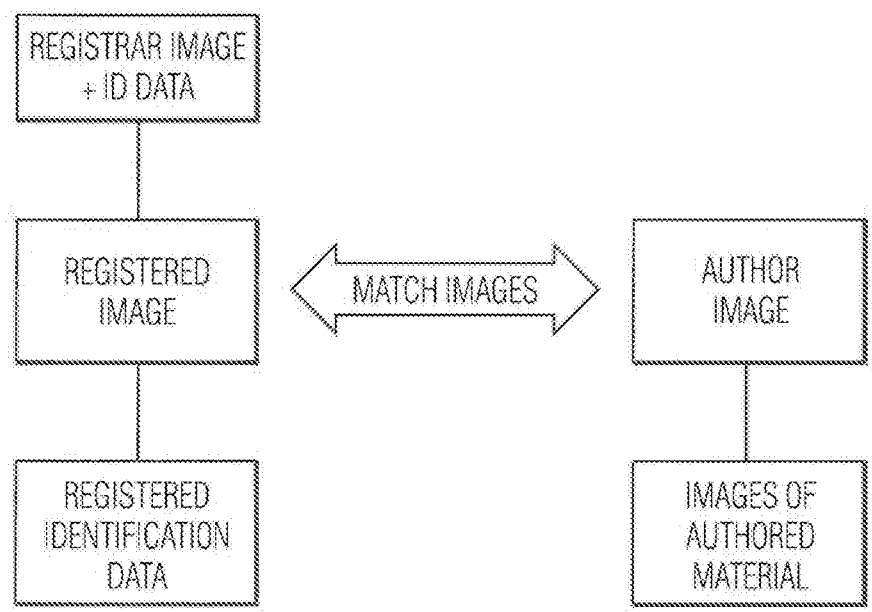
FIG. 11 shows a schematic diagram which illustrates the concept underlying the invention when the image of a registrar is captured at the time of the registration step.

Another method of enhancing security during the registration step is shown in FIG. 11, a schematic analogous to FIGS. 1 and 10. In this embodiment, the image of a biological identifier of the registrar (obtained kith apparatus such as that shown in FIGS. 3 through 6) and the image of the registered person are merged into either a single file or a single image. Alphanumeric identification of the registrar would be included in the composite file.

Figure 12:
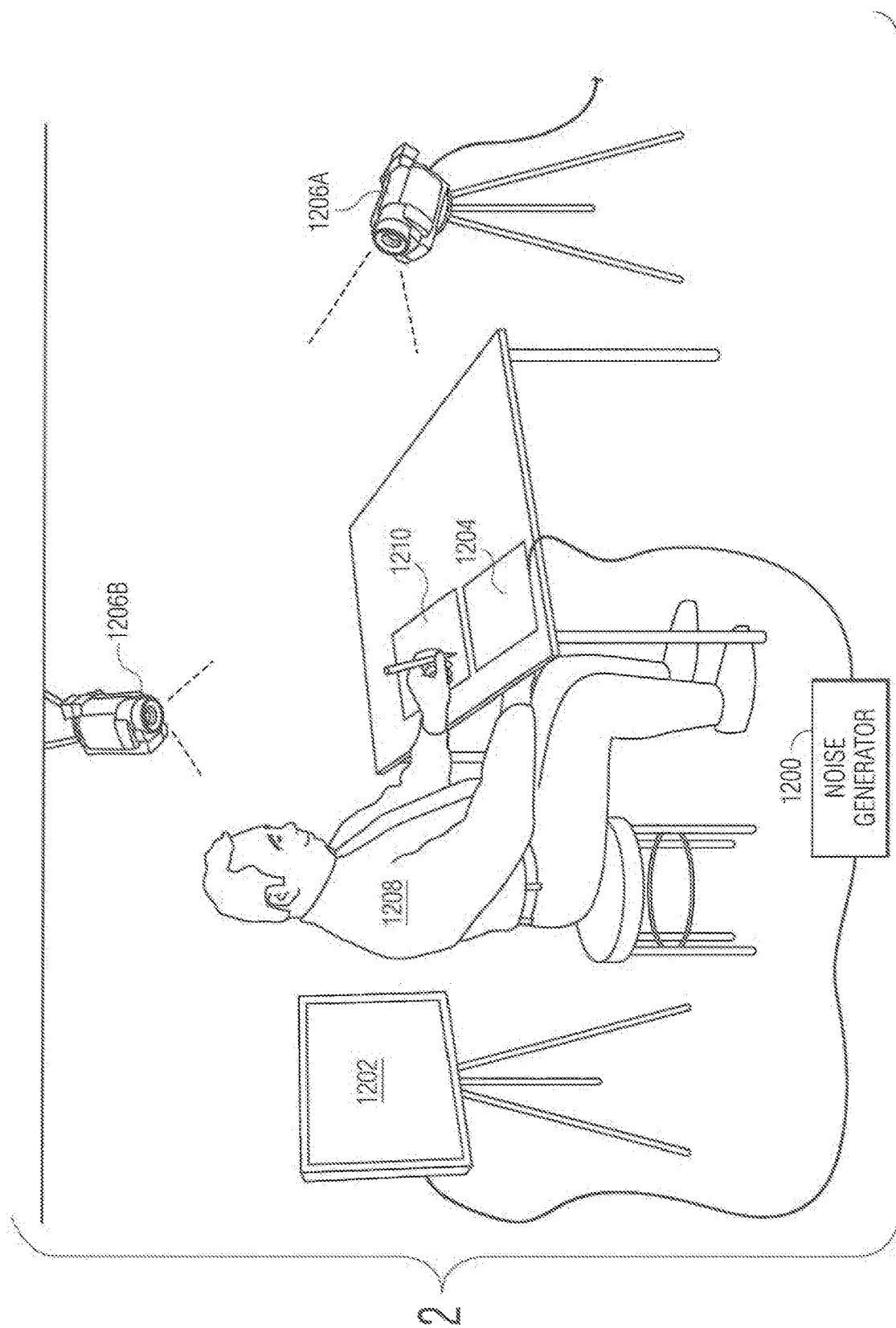
FIG. 12 shows a representational diagram of apparatus for using two identical representations of noise on each of two video screens to document that the recordings of two different cameras have been performed simultaneously.

FIG. 12 shows a method of demonstrating the simultaneity of recording of two video images on separate cameras. A noise generator 1200 generates a random, highly complex pattern, continuously changing pattern which is identically and simultaneously displayed on video screens 1202 and 1204. These screens are placed so that they may be recorded by a video camera along with the other material to be recorded by that camera. Thus camera 1206A simultaneously records both the face of person 1208 and the highly complex, continuously changing pattern on screen 1202. Camera 1206B simultaneously records the text material 1210 written by 1208 and the complex video images on 1204 (which are identical to the images on 1202). Since the task of duplicating the complex and continuously changing pattern of images displayed by 1202 and 1204 would be extremely arduous, it would make attempting to corrupt one of a pair of simultaneously recorded images (e.g. by substituting a different face), extremely difficult or impossible. 1200 may generate any one of a number of forms of very complex pattern including white noise, other noise, or even a repetitive pattern of extreme complexity.

Figure 13:
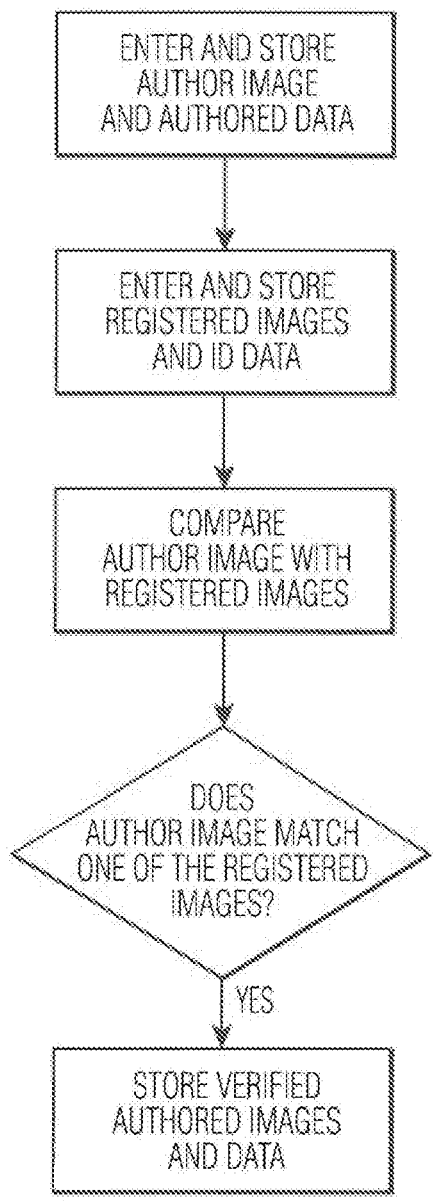
FIG. 13 shows a flow diagram of the steps followed in an alternate embodiment of the invention.

FIG. 13, analogous to FIG. 2, shows a flow diagram of another embodiment of the invention, in which the order of registration (block 200 in FIG. 2) and authorship (block 202 in FIG. 2) is reversed.

The concept of linking a particular person to a particular body of information has, hereinabove, been considered with respect to providing a strong linkage between provided information and the person providing the information. Hereinbelow, the concept and invention is presented with respect to providing a strong linkage between provided information and the person requesting the information. It will be clear that such a strong link will be useful for (a) providing secure communications, (b) for preventing access to information stored in a computer memory or other digital device by an inappropriate person, and (c) for preventing the modification of information stored in a computer memory or other digital device by an inappropriate person.

Figure 14A:
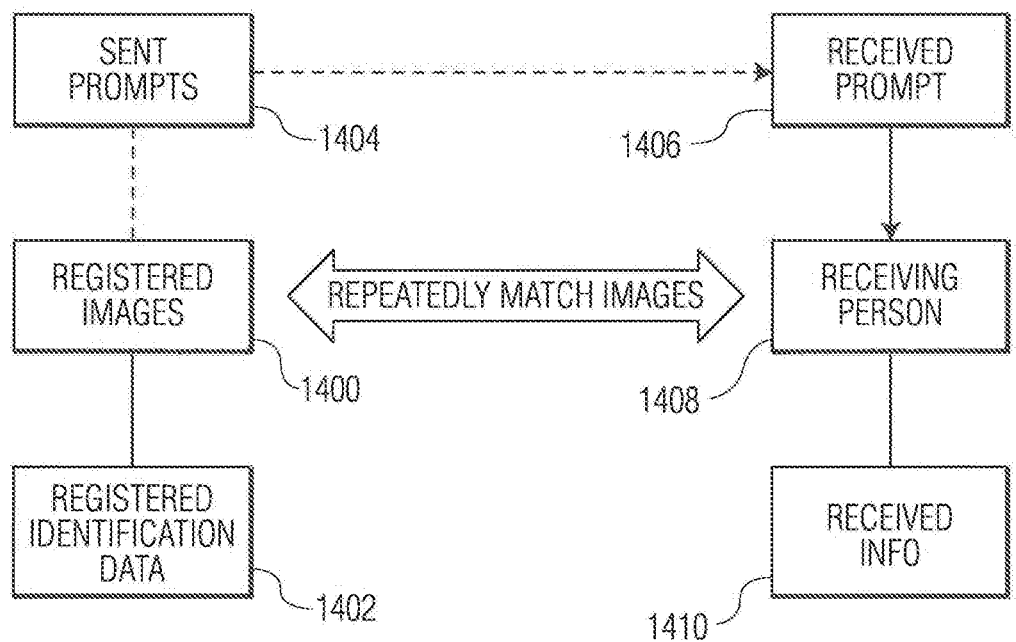
FIG. 14A is a block diagram, similar to FIG. 1, is a block diagram which illustrates the basic concept underlying another aspect of the present invention.

FIG. 14A shows the conceptual basis of an invention which identifies a person requesting to receive information, ("RP") by:

(a) repeatedly examining a biologic feature of the person and comparing it to information in a database which contains files which comprise (i) information pertaining to the details of the biologic feature of a registered person, the information having been obtained under a plurality of different conditions, and (ii) alphanumeric identification [e.g. name, social security number, date of birth, etc. are also stored in correspondence to the biologic] of the registered person; and (b) providing a prompt which induces a change in the appearance of the biologic identifier.

By providing a prompt which alters the appearance of the identifier, and by repeatedly observing the identifier, the invention provides a far more secure system than the static approach, known in the art, of simply comparing an image of a biologic identifier ("BI") of a person requesting access to a digital system to file images. An example of the static approach is described in U.S. Pat. No. 8,189,096 to Azar.

Defeating the static approach, i.e. compromising a computer or communication system protected by the requirement of providing a static image, entails (i) obtaining and storing a BI image, during a process that is perhaps unknown to the person associated with the BI, and (ii) providing the previously stored image of the BI, at a time when information or computer system access is desired by someone who is not the person associated with the BI [i.e. an inappropriate person ("IP")], but who is in possession of and can provide the information contained in the static BI.

The static system becomes harder to defeat if multiple (static) images must be provided to gain access to the system. But it still may be defeatable by an IP, by obtaining a multiplicity of static images of the BI of a person registered to use the system.

In one embodiment of the current invention, advantage is taken of the ability to change the appearance of a BI upon the request of the person or system providing secure information or desiring secure communication. A simple approach is a voluntary request to the RP to perform a motion which results in a change in the appearance of that person's BI. Examples of such changes include a request to turn the RP's face in one direction or another, to wink one eye, to look to the right, left, up, down, etc. (with or without moving the head) or to move a finger containing a fingerprint in a particular way, or a palm containing a palm print or a pattern of blood vessels in a particular way.

Still other requests may involve moving one part of the body containing one BI so that its relationship with another part of the body containing another BI is geometrically altered. The value of such a voluntary prompt is that the nature and timing of the request is entirely under the control of the information source ("IS"), whether the source is a person or a computational device.

Still other requests may be for the RP to follow a moving point or object on a display screen, using apparatus in which the IS controls the trajectory of the point on the screen, while a camera observes the user eye motion, iris image, retinal vein image, image of blood vessels on the surface of the eye, or facial motion. Although the tracking of such a point by the RP would not perfectly match the apparent motion of the point, software methods to compensate, and statistical techniques to assess a match could be applied as are known in the art. Clearly, attempts by an IP to communicate inappropriately with such a system would be extremely difficult, requiring the IP to very quickly provide a sequence of BI images which match a not previously expected pattern of variance. By making such the choice and timing of prompts random or pseudo random (e.g. by using a variety of techniques to generate such random information including the digitization of white noise, the use of minutae related to sports information [e.g. number of milliseconds between pitches in an ongoing baseball game], stock market minutae [e.g. ongoing trades and their timing], astronomic information [e.g. solar activity], traffic information minutae [patterns of people walking through Times Square], by electronically generating pseudorandom number patterns), the task of the IP becomes more difficult.

Figure 15:
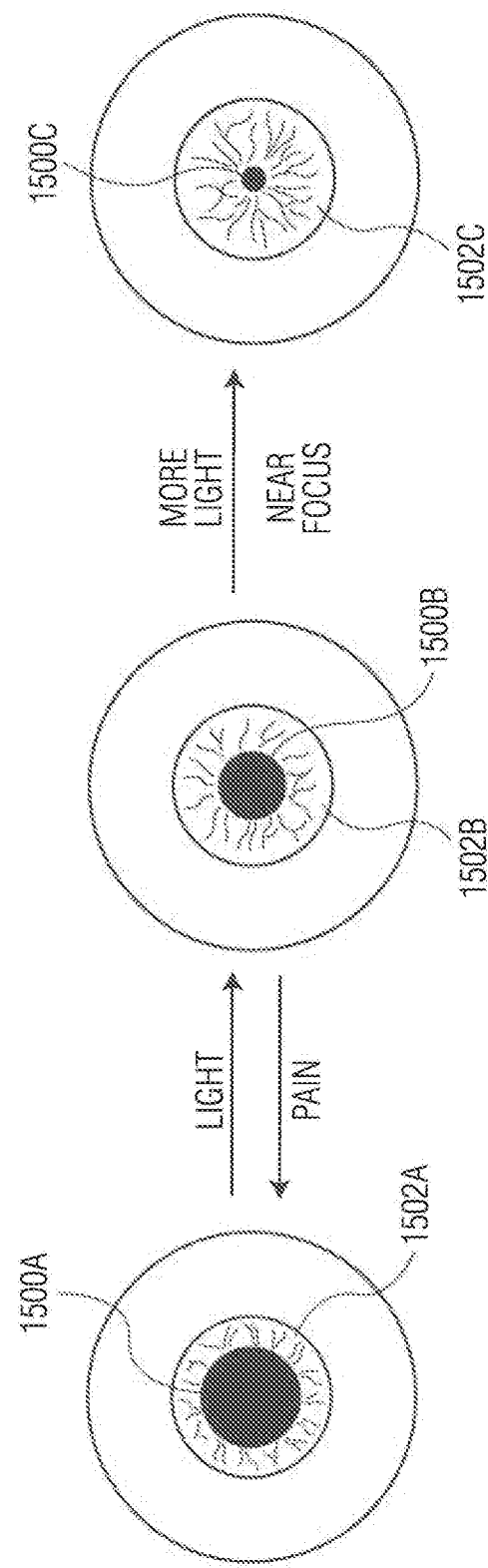
FIG. 15 is a representation of the functional aspect of the human iris.

A still greater burden on the inappropriate person attempting to gain access entails the use of prompts resulting in entirely involuntary physiologic actions. One such example is the application of light to the human eye. As shown in FIG. 15, the pupil 1500A-C, an opening in the iris 1502A-C, constricts in response to light in a graded fashion over a certain range, i.e. more light impinging on the eye causes more constriction of the pupil/"enlargement" of the iris, which in turn is mediated by muscular tissue within the iris. This process causes a change in the appearance of the iris. Since the iris is a known biologic identifier, the application of light to the eye will produce a change in the details of the iris pattern. Thus any one individual will have nearly limitless possible iris patterns, which can be obtained by a change in the amount of incident light.

In turn, the extent of incident light may be controlled by apparatus at the information source. Prompts can control the light intensity, the wavelength, the spatial placement of the light, the size of the light source, the number of light impulses, the time interval between impulses, the duration of each impulse, etc. Furthermore, the IS may store prompt details and generate and expected iris response for comparison with an observed one. Furthermore, the IS may generate linear and other combinations of iris images stored in a computer database, thereby potentially expanding the database limitlessly. The IS may also adjust the amount of applied light to attempt to match an iris image on file.

In addition, alteration in iris size may be induced by having the RP change focus from a distant object to a near one (which may be presented on a computer or digital device display screen), or vice versa. In addition, dilation of the pupil/constriction of the iris may be induced by a painful stimulus, which may be applied to the RP under remote control via a device attached to the patient (e.g. one which provides a mild electric shock).

A given induced change in iris image, (i.e. the varying biologic identifier,) may not always occur identically for a given amount of light. The system administrators and architects will overcome this by either (a) storing a variety of responses to each prompt, obtained during a registration period for the person who is to be an authorized user of the system, (b) utilizing linear or other combinations of previously observed responses by a particular user, or (c) by utilizing neural networks to learn the patterns of authorized system users.

The pupil/iris changes, in turn, will change the appearance of another BI, the pattern of retinal blood vessels. A constricted pupil narrows the area of retinal surface (and vascular pattern) available for view, while a dilated pupil has the opposite effect. Thus another embodiment of the invention entails RP identification using retinal vessels as the BI, and prompts cause a change in iris/pupil geometry which changes the viewable retinal field.

The aforementioned involuntary changes in the appearance of the BIs caused by IS prompts in essentially unpredictable manner would create a situation that would be extremely difficult for an IP to defeat.

Referring again to FIG. 14A, registered images of the BI 1400, each linked to alphanumeric identification data 1402 of a person authorized to access the system ("AP") are stored in a database. If a RP requests access to the system, information from the system, or the ability to communicate a person using the system, prompts are sent 1404, received 1406 and applied such that upon interacting with RP 1408, the prompts alter the BI. Images of the RP 1408 are repeatedly compared with registered images 1400, to determine if the RP is an AP. If the RP is determined to be an AP, as a result of repeated biologic ID match during the application of one or more prompts, then information 1410 may be exchanged with, or sent to the requesting person.

FIG. 16A shows one embodiment of apparatus for the aforementioned prompt-based security system. AP identifying information is stored in and accessed from database 1600 by processor 1602. Prompts may be generated in a variety of ways, as indicated hereinabove, including the digitization of white or other noise input from generator 1606, the digitization of information related to random or almost-random events inputted at 1608, by a random or pseudorandom number generation program which runs on processor 1602, or by inputted audio prompts 1610. The processor outputs a signal to prompt generating device 1612, which may be a screen which displays digital information 1612, a sound producing device 1614, a light producing device or a pain producing device. Camera 1616 is oriented to view the biologic identifier (e.g. iris pattern, retinal veins, etc.) of RP 1618 in detail. 1616 supplies repeated images of the BI of the RP to processor 1602. 1602 compares these received images to the database 1600. The results of the comparison may be indicated by either (a) a numeric or graphic indication of the degree of correspondence between the 1618—derived images and the database images, (b) an indication that a threshold has been exceeded for declaring a match between the RP and an AP, and/or (c) the allowance of access to information in computer memory 1620. Information is input to 1620 by input device 1622. Information obtained, following the allowance of access, may be stored in information storage device 1626.

As indicated hereinabove, the certification that AP information stored in 1600 is indeed correct may be accomplished by utilizing a registrar, i.e. a registration person who is authorized to input information to 1600. This input occurs via input device 1624, which may also input alphanumeric and/or biologic identification information pertaining to the registrar.

Figure 16B:
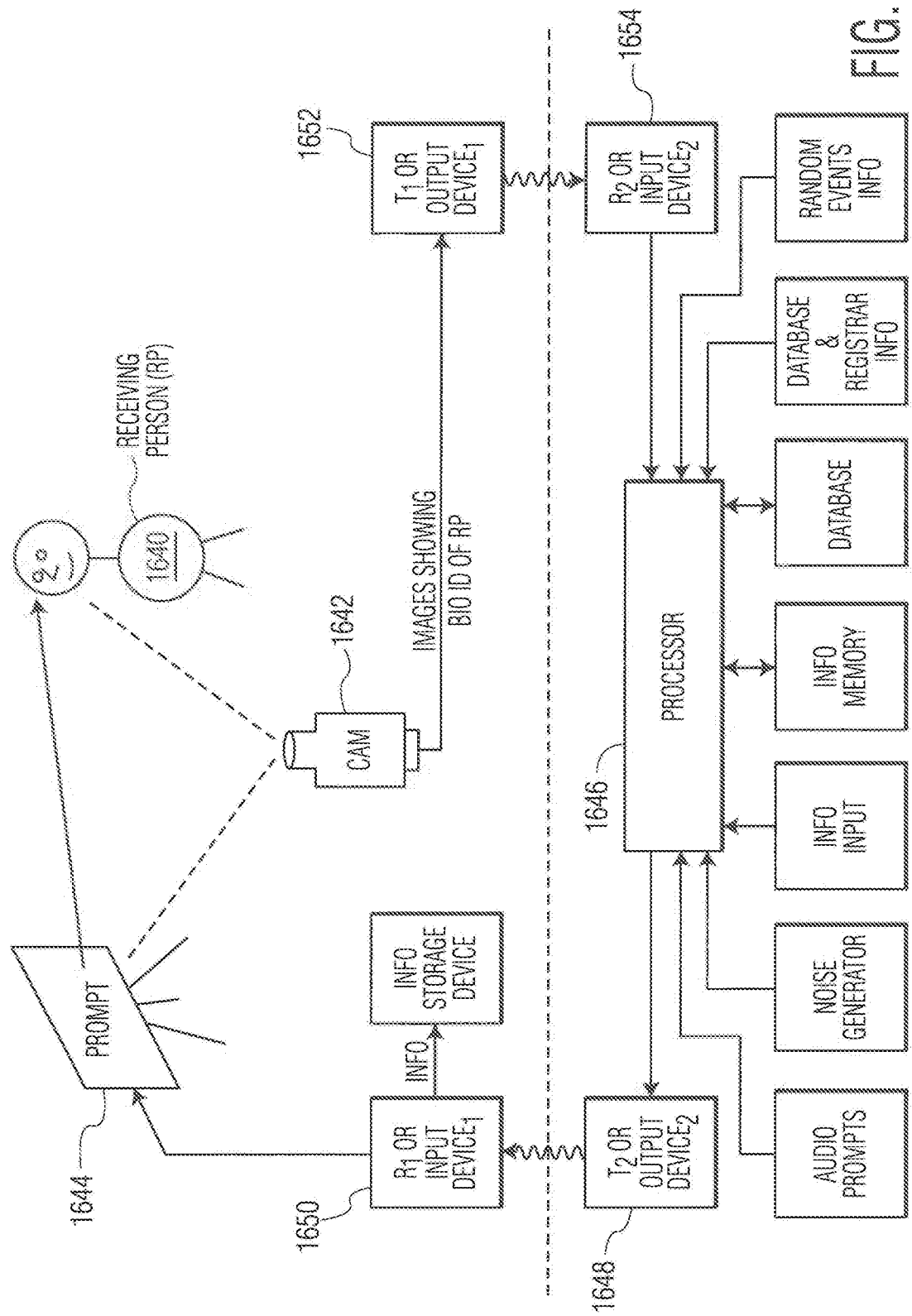
FIG. 16B is another block diagram of apparatus in a second preferred embodiment of the invention.

Whereas the connections between (i) processor 1602 and (ii) each of camera 1616 and prompt device 1612 comprise a wired connection or a series of wired connections, FIG. 16B shows embodiment of the invention in which camera 1642 and prompt producing device 1644 are in communication with processor 1646 by wireless means. The link from 1646 to 1644 is via transmitting device or output device 1648 and receiving device or input device 1650. The link from processor 1646 to camera 1642 is via transmitting device or output device 1652 and receiving device or input device 1654. 1648 and 1654 may comprise a single transmitting and receiving device. 1652 and 1650 may comprise a single transmitting and receiving device. A wide variety of such communication devices and methods will be known to those skilled in the art. Combinations of wired and wireless links for the system, which embody features of each of FIGS. 16A and 16B are possible as well.

Communication between (i) the processor 1646 and (ii) each of camera 1642 and prompt device 1644 may be by a public or private telephone network, the internet, a private digital or analog communication network, radiofrequency communication (including the microwave portion of the spectrum, and Bluetooth communication), satellite-based communication, light communication (including infrared and ultraviolet), communication by modulated magnetic fields, and communication by sound, ultrasound, or subsonic longitudinal wave modulation means.

RP 1640, camera 1642 and prompt device 1644 may be situated in a location which is different, and possibly remote from processor 1646, and its associated input devices and memory devices. Such a separation between the corresponding elements of FIG. 16A is also possible.

Each of the remaining elements in FIG. 16B is functionally the same as the corresponding element in FIG. 16A, described hereinabove.

FIG. 16C is functionally similar to 16B, except the input/output—transmitting/receiving devices have been replaced by a communication system. In addition, each of camera 1674, prompt device 1678 and storage device 1680 are linked to the system via a second processor 1672.

As is known in the art, each processor 1670 (which is analogous to processor 1646 in FIG. 16B) and 1672 will be linked to interface elements, to facilitate the exchange of information with the system. The methods and means of communicating through the system are those stated in conjunction with FIG. 16B. The relative locations of each processor and its linked elements (e.g. camera 1674 and RP 1676, in the case of processor 1672), are also conceptually parallel to the situation described in conjunction with FIG. 16B.

Although FIGS. 16A, 16B and 16C each show different means of linking the prompt producing and image analyzing processor (e.g. 1602, 1646 and 1670) to the respective prompt producing device and camera, these Figures all pertain to a common invention.

FIG. 16C also shows an audio output device 1682 for delivering audio prompts from input device 1686. It also shows a pain producing device 1684, attached to the body of the RP, which may provide a shock, heat or other noxious stimulus.

Figure 18:
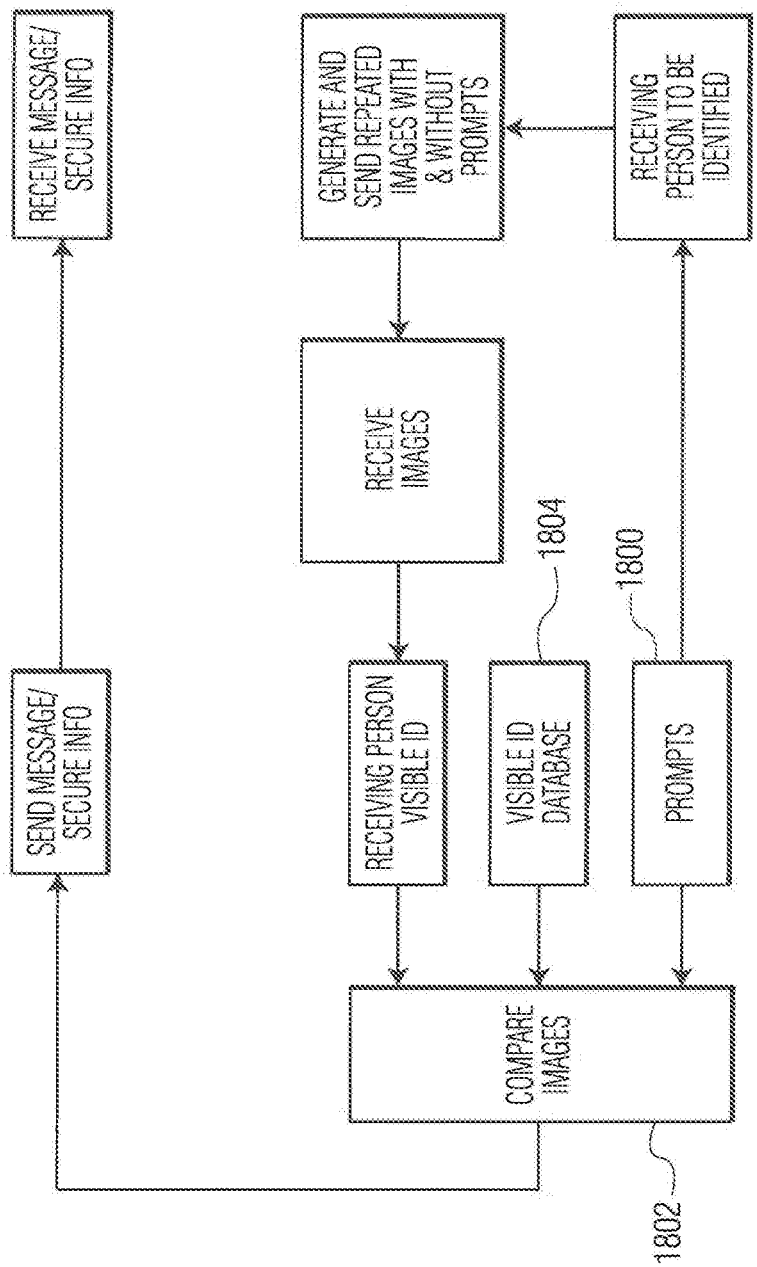
FIG. 18 is a block diagram showing the operation of the apparatus in FIGS. 16A, 16B and 16C.

FIG. 18 shows a block diagram indicating the function of the prompt-based embodiment of the invention. It has been fully described in conjunction with the specification of FIGS. 14A, and 16A-C. The nature and timing of prompts 1800 may be utilized for comparing images 1802, since clearly it would be advantageous for the processor to indicate a proper correspondence between prompt and observed change in BI. For example, the observation of a pupil which dilates in response to a light stimulus, even if associated with observed iris images before and after the stimulus which match those in the database, would call into question the veracity of the identification.

Visible ID database 1804 may also contain biologic ID images which show a body part from a variety of vantage points and angles.

Figure 17A:
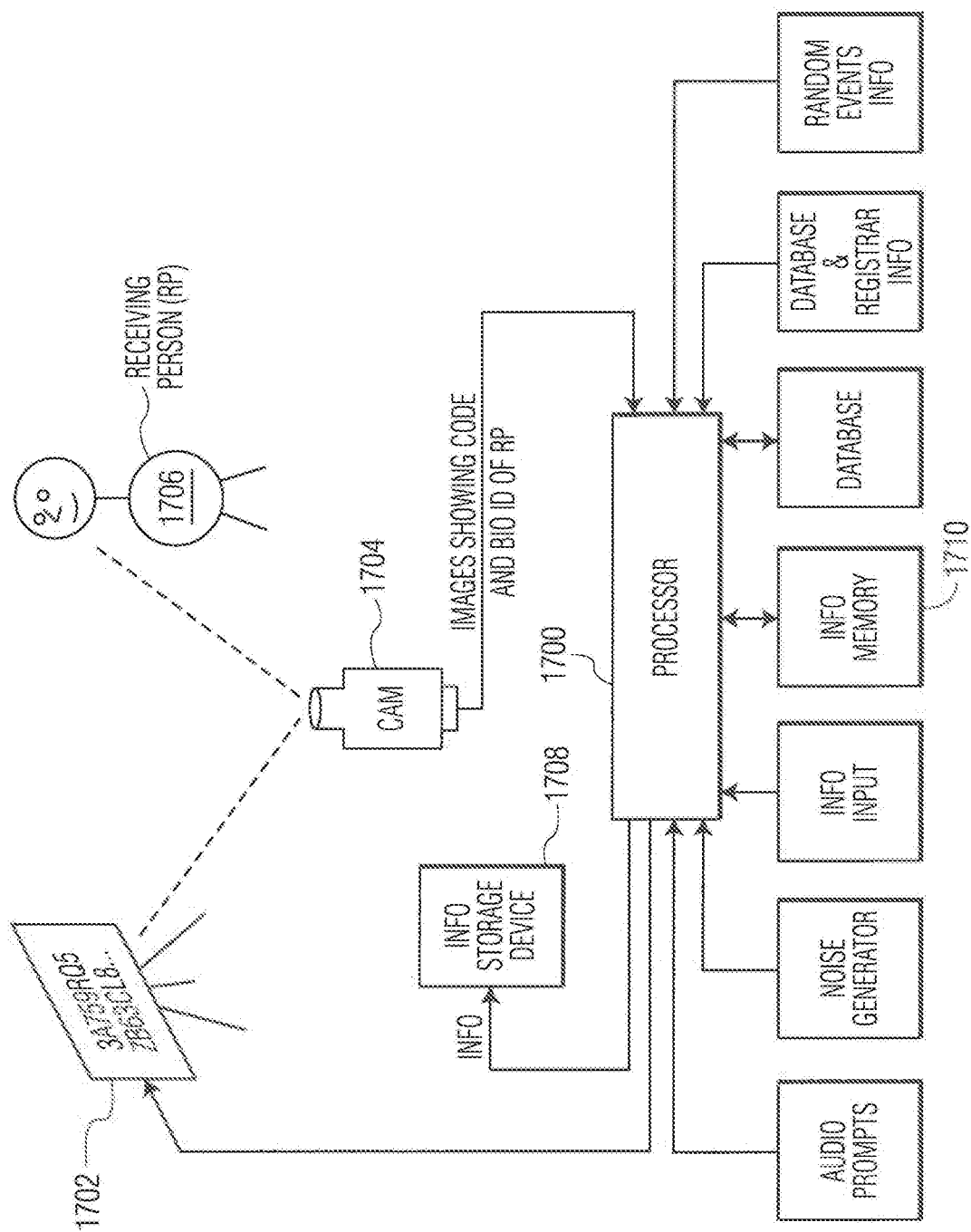
FIG. 17A is a block diagram of apparatus in a third preferred embodiment of the invention.

Another approach to further increasing the security and accuracy of identification of a user, and the location of the user of the system is shown in each of FIGS. 14B, 17A-C and 19. Referring to FIG. 17A, the apparatus differs from corresponding FIG. 16A, in that processor 1700 is operative to generate a code and to produce a signal which causes display screen 1702 to display a visual representation of the code. Camera 1704 is situated to view both screen 1702 and the BI of RP 1706, to produce a composite image containing both the BI and the screen image of the code. Processor 1700, on receipt of the composite image extracts each of the code image and the RP image. It compares the code image with a stored version of the sent code, and it compares the Bio ID image with data in its database. It then can (i)

indicate a numerical or graphical presentation of the extent of match of each of the two composite image components, (ii) indicate whether each or both has met or exceeded a threshold deemed to be satisfactory, and/or (iii) allow the passage of information to storage device 1708 from information memory 1710.

It is to be understood that each step in the passage of the information reflected by the code may involve a degree of distortion/degradation of the information. The conversion of the information from digital signal to visual display is one such step, as is the conversion of the screen information to a camera image, and the conversion of the camera image to a camera signal. Further losses of integrity may occur during each limb of signal transmission from and to the processor. Thus the analysis of the received code by the processor, and its comparison with the sent code will result in a less than perfect match even when system integrity is uncompromised. Algorithms for assessing the goodness of fit of the received version of the code information to the sent version will be apparent to those skilled in the art.

The difficulty of having an inappropriate person gain access to processor 1700 is enhanced by including the code component in the composite image: Gaining such access would require the IP to be able to reproduce the BI and reproduce the image of the code, and to do so within a single image. The difficulty of such reproduction is enhanced by rapidly changing the code. Each of the elements (the noise generator, the random outside events information and the processor itself) utilized to generate random and pseudorandom variations discussed in conjunction with FIG. 16A, is utilized in FIG. 17A to generate such variations in the code.

This variation may utilize either a single image of biologic ID/code image or repeated ones. In addition, a prompt producing device and activation means (not shown in the Figure), could be added to further augment the degree of security.

Each of the remaining elements of FIG. 17A is analogous to the respective element in FIG. 16A.

Figure 17B:
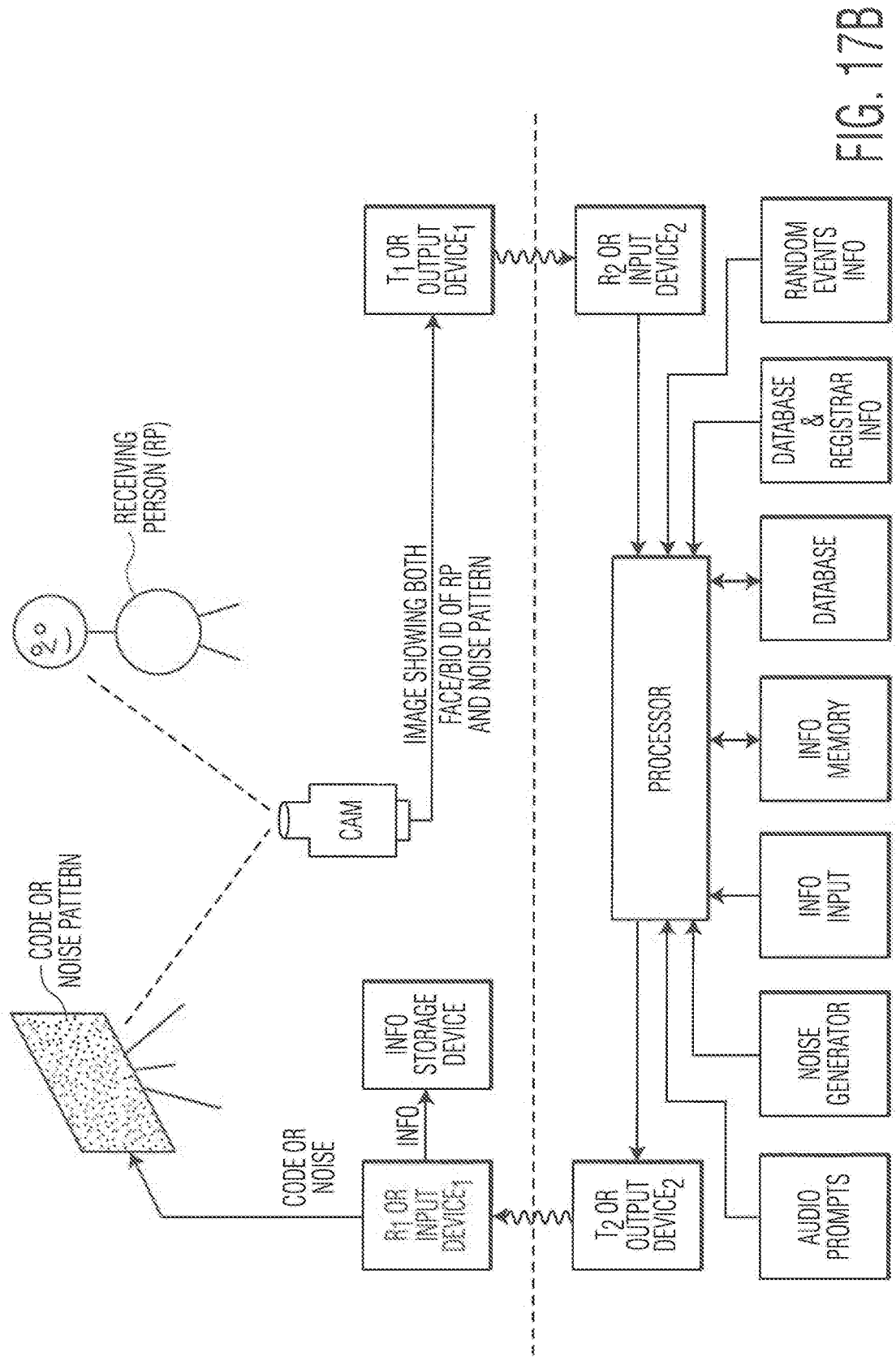
FIG. 17B is another block diagram of apparatus in a third preferred embodiment of the invention.

FIG. 17B is analogous to FIG. 16B, in that both show a wireless mean for communicating between the (i) processor, and (ii) the items in the vicinity of the RP (which in the case of FIG. 17B are the camera and the code display screen.

Figure 17C:
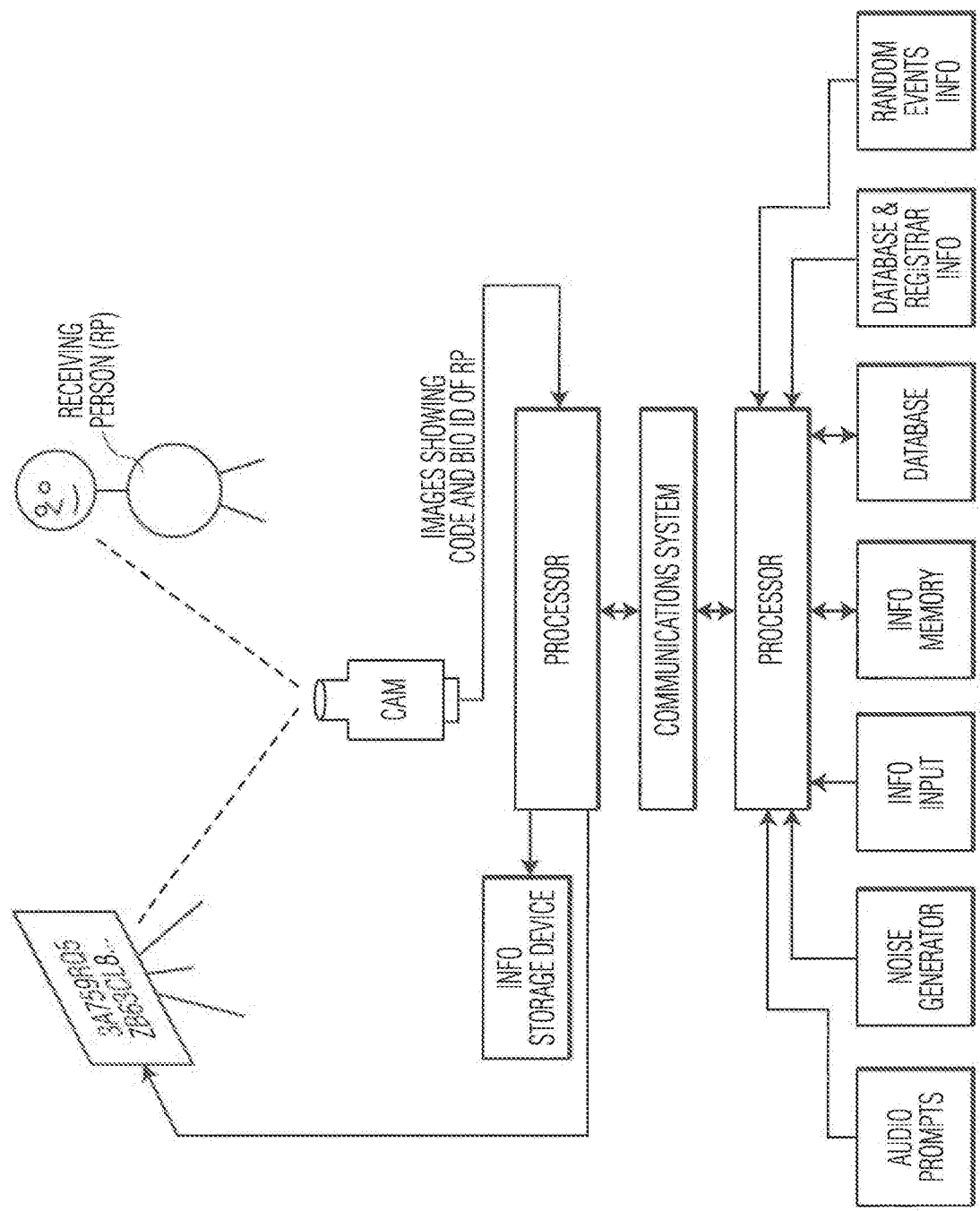
FIG. 17C is yet another block diagram of apparatus in a third preferred embodiment of the invention.

FIG. 17C is analogous to FIG. 16C. It shows the embodiment of the invention with composite images of both code and BI, and a communication system linking the first processor with camera, information storage device and screen via a second processor.

Figure 19:
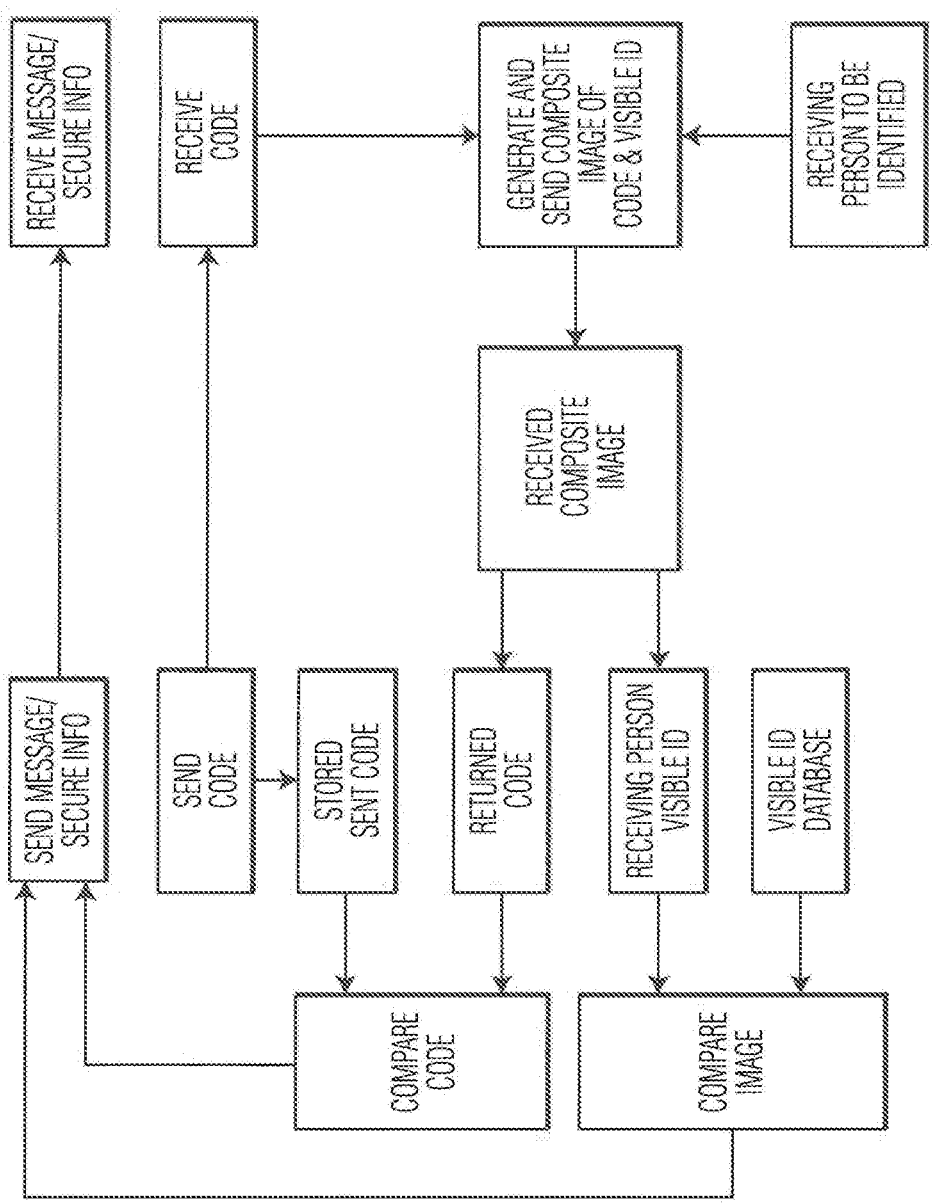
FIG. 19 is a block diagram showing the operation of the apparatus in FIGS. 17A, 17B and 17C.

FIG. 19 shows a functional block diagram of the operation of the apparatus in FIGS. 17A-17C. The block diagram is analogous to that of FIG. 18, for the prompts version of the invention.

Figure 14B:
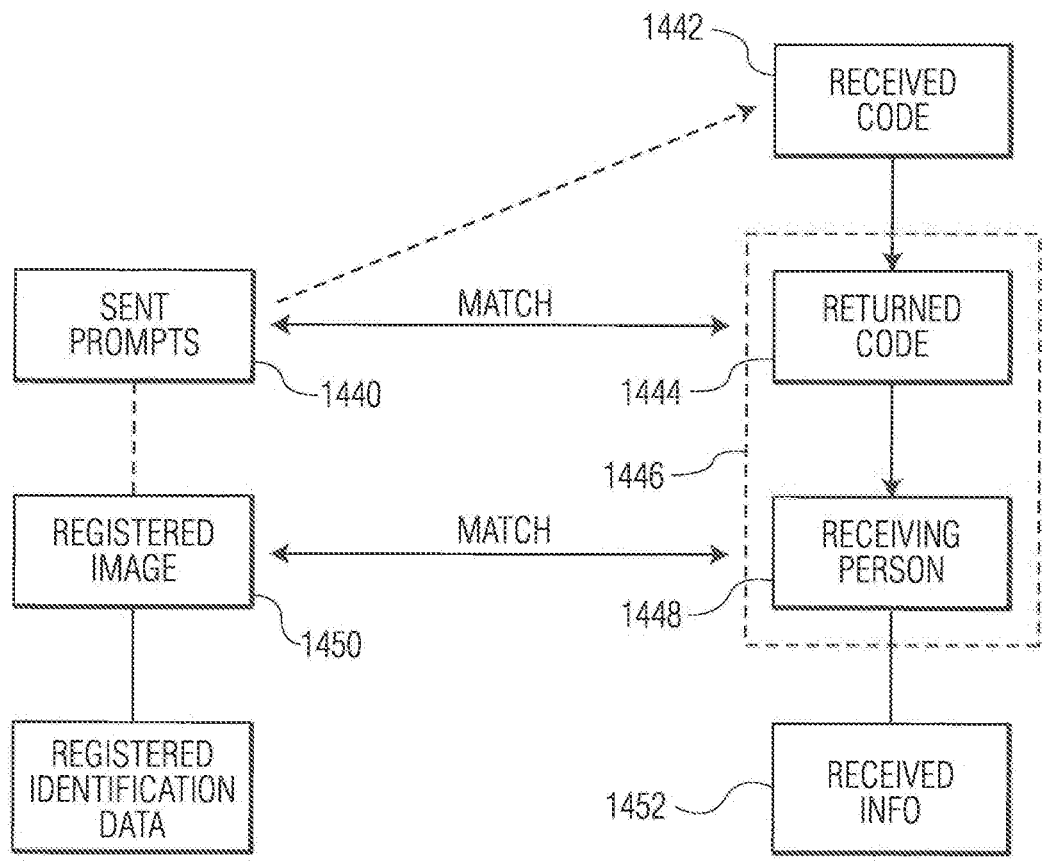
FIG. 14B is a block diagram, similar to FIG. 14A, is a block diagram which illustrates the basic concept underlying yet another aspect of the present invention.

FIG. 14B shows the conceptual basis of the composite image version of the invention, and is analogous to FIG. 14A for the prompts version of the invention. Sent code 1440, arrives at the RP site as received code 1442 and is incorporated into composite image 1446 and is extracted from the image as returned code 1444. The information in 1444 is compared with that of 1440, to assess the extent of match. In addition, the extracted bio ID image 1448 is compared to the database image 1450. If the comparisons are satisfactory, information may be received 1452 by the RP.

Figure 20A:
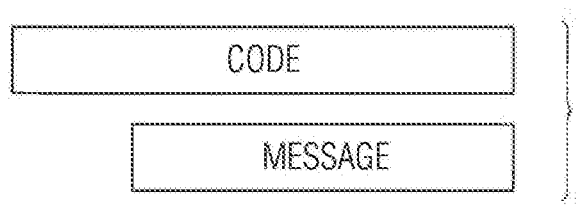
FIGS. 20A and 20B are schematic diagrams showing the composition of information sent to a receiving person.
Figure 20B:
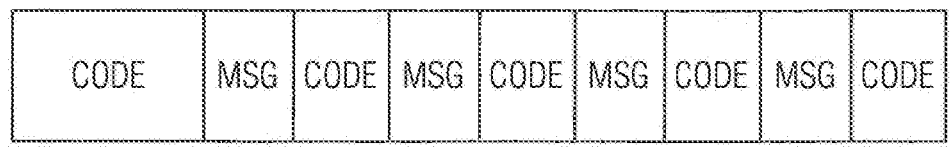

FIGS. 20A and 20B show schematic representations of how code and message may be arrayed, for versions of the invention which use the code matching procedure. In both Figures, the transmission of code precedes the transmission of a message or information containing secure information. In FIG. 20A, once a period of code transmission indicates a satisfactory information exchange, the message and code are each transmitted in parallel fashion. Any interruption in code match results in interruption of the message. In FIG. 20B, the process is incremental: a code segment is followed by a message segment; then the process repeats. A failure to match properly at any point results in interruption of the message.

Figure 21A:
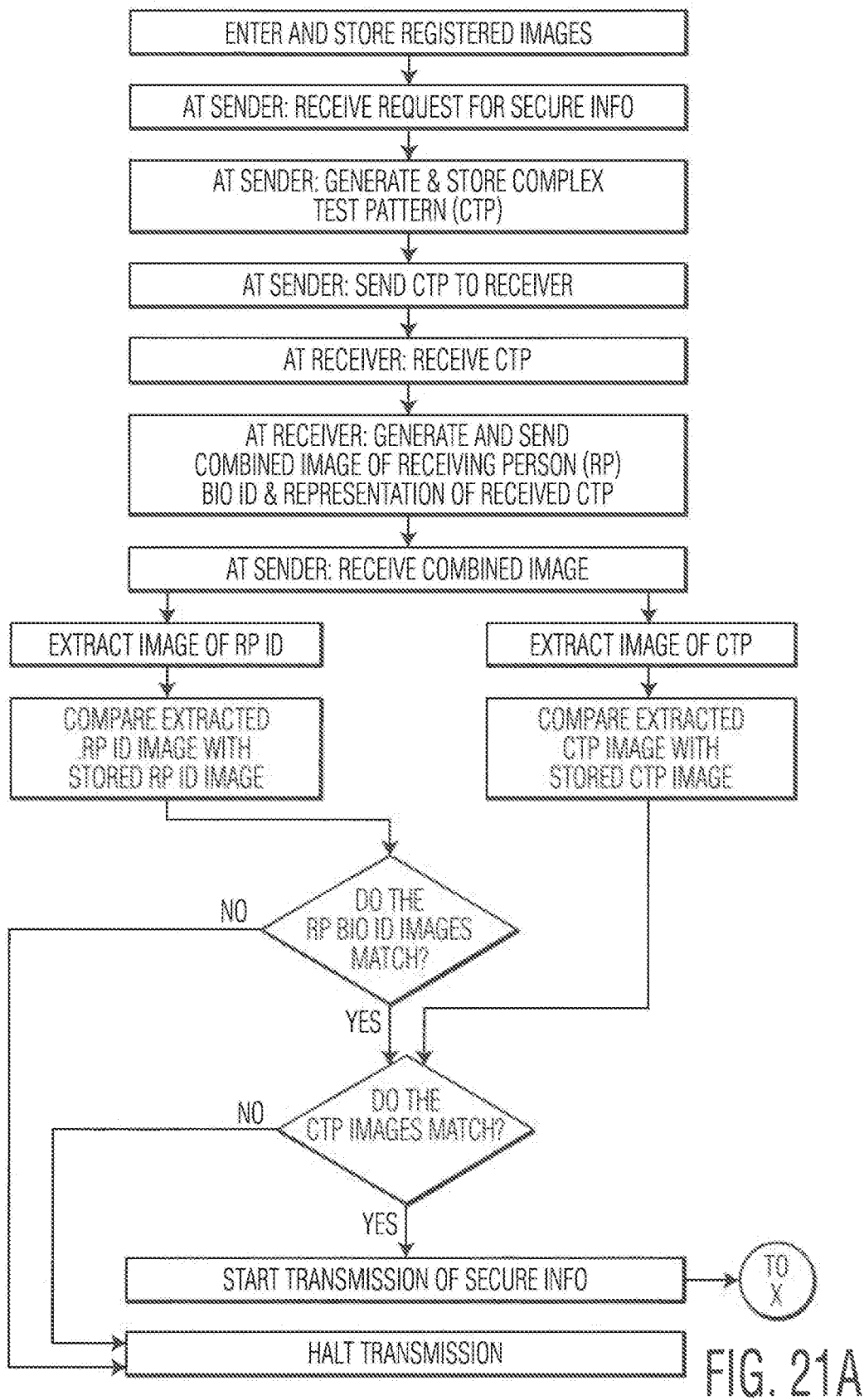
FIGS. 21A and 21B are a flow diagram showing the operation of the apparatus of FIGS. 17A, 17B and 17C.
Figure 21B:
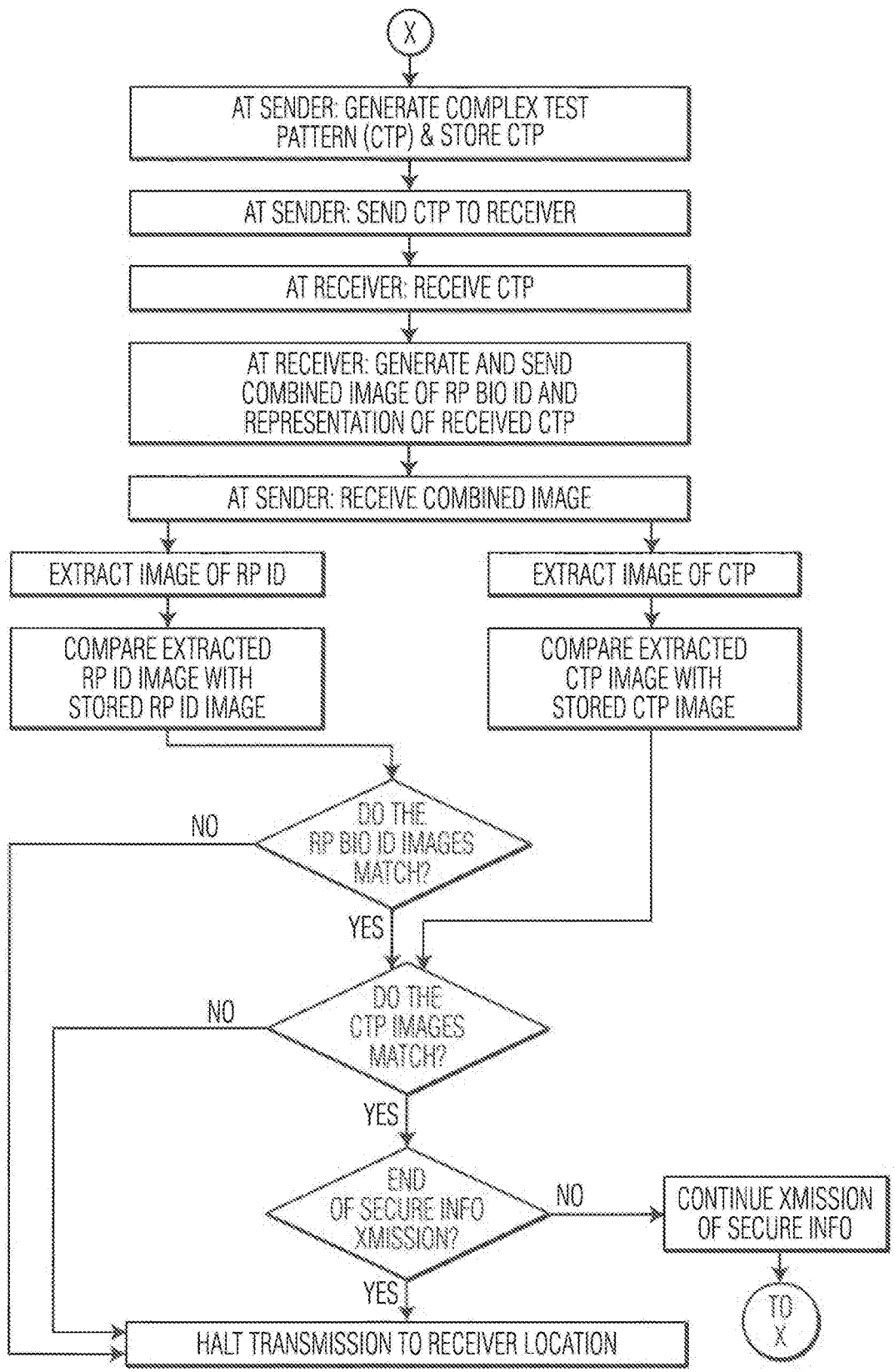

A flow diagram of the algorithm which embodies the schematics of FIGS. 20A and 20B is shown in FIGS. 21A and 21B.

Figure 22A:
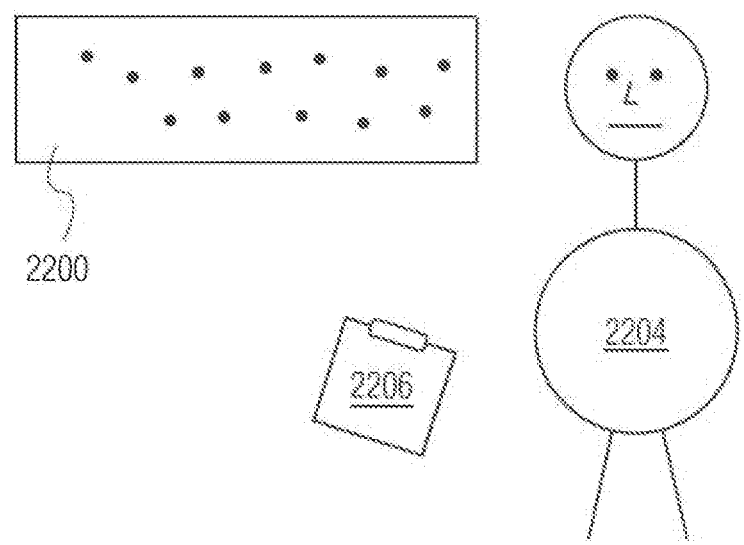
FIGS. 22A-22D are representational diagrams of apparatus for the simultaneous viewing of code information and an identifying biologic feature.
Figure 22B:
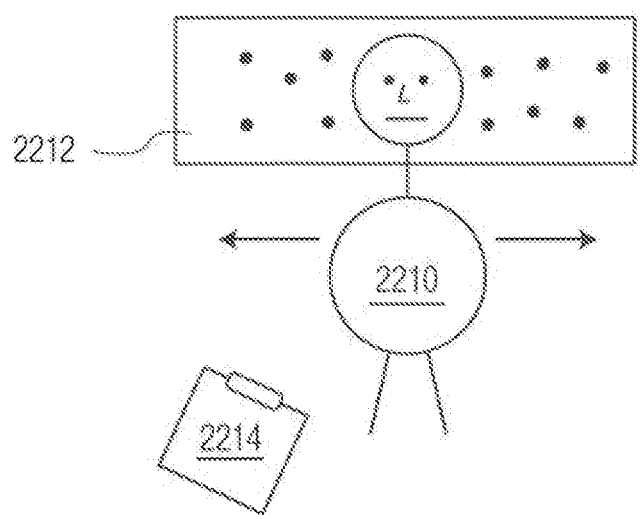

FIGS. 22A-22D show various configurations for merging the screen which shows a representation of the code, and a visible biologically unique feature of a person requesting receipt of information. In FIG. 22A, screen 2200 (in which the code representation is indicated by an array of randomly placed dots) is next to RP 2204. The iris, retinal vessels, face or other body part of 2204 is imaged with screen 2200 by camera 2206. In FIG. 22B, RP 2210 is situated in front of screen 2212. The scene is imaged by camera 2214. RP 2210 may receive prompts instructing the RP to move to the right or left, to move closer to or further away from 2212, etc. Having information about the spatial relationship between the camera 2214 and each of the RP and the screen allows the processor to calculate which portions of the imaged code become obscured or visible as the RP carries out the prompt instructions.

Figure 22E:
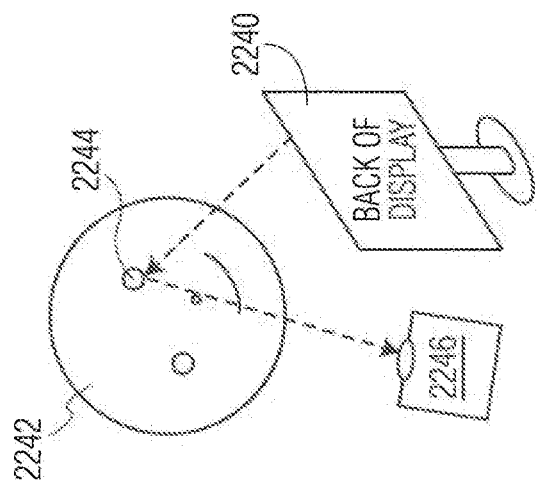
FIG. 22E is a representational diagram of apparatus for projecting information onto an organ comprising an identified biologic feature, and thence to a camera.
Figure 22D:
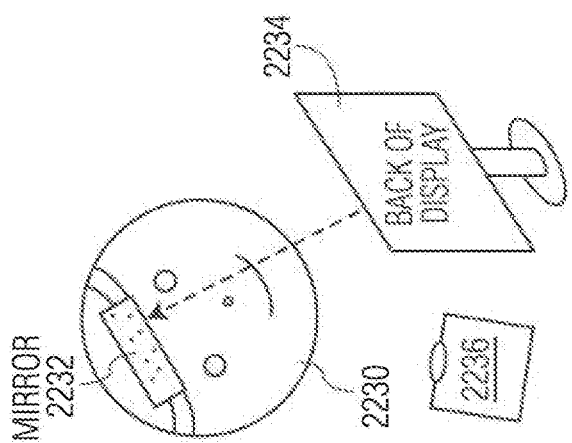
Figure 22C:
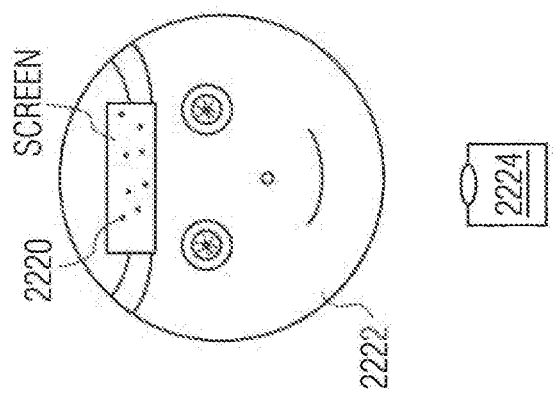

Yet another technique for merging the code screen and the BI is shown in FIG. 22C. Screen 2220 is wearable, attached to the head of RP 2222 by a headband. Camera 2224, pointed at the face of the RP can image the screen and either the iris, retinal vessels, face, skin quality, etc. of the RP.

FIG. 22D shows RP 2232 wearing a reflective surface—e.g. a mirrored item—above the eyes. The surface reflects the contents of screen 2234, on which the code would be displayed (code not seen because the back of screen faces the reader). Camera 2236, like camera 2234 in FIG. 22C images both the BI and the screen contents.

In the aforementioned detailed description of each of FIGS. 14B, 17A-C, 19, 20, 21A-B and 22A-D, the screen contents have been stated to be a representation of a code. However, an embodiment of the invention in which the screen contents are a message to the RP is also possible. Yet another variation is an embodiment in which the screen contents comprise a mixture of a message and a code. In some if not many cases, these arrangement will be considered to be less desirable because the verification process would require two-way transmission of the message: i.e. (a) from the processor to the screen, and (b) back to the processor as part of the composite image.

Although a two way version of the invention is possible, in which two people communicate each having a respective RP camera and display screen (or RP camera and prompt producing device), and each having a respective processor for analysis of the aforementioned matches, the two way transmission would increase the chance of interception and/or diversion of the message.

An additional means of security entails projecting a code image onto a reflective portion of the eye of the RP, and then imaging the reflected image. This is shown in FIG. 22E, in which display device 2240 projects a code image onto the eye 2244 of RP 2242, which is then imaged by camera 2246. This allows for especially close linkage of BI ID and code image, since both concern the eye of the RP.

Figure 23:
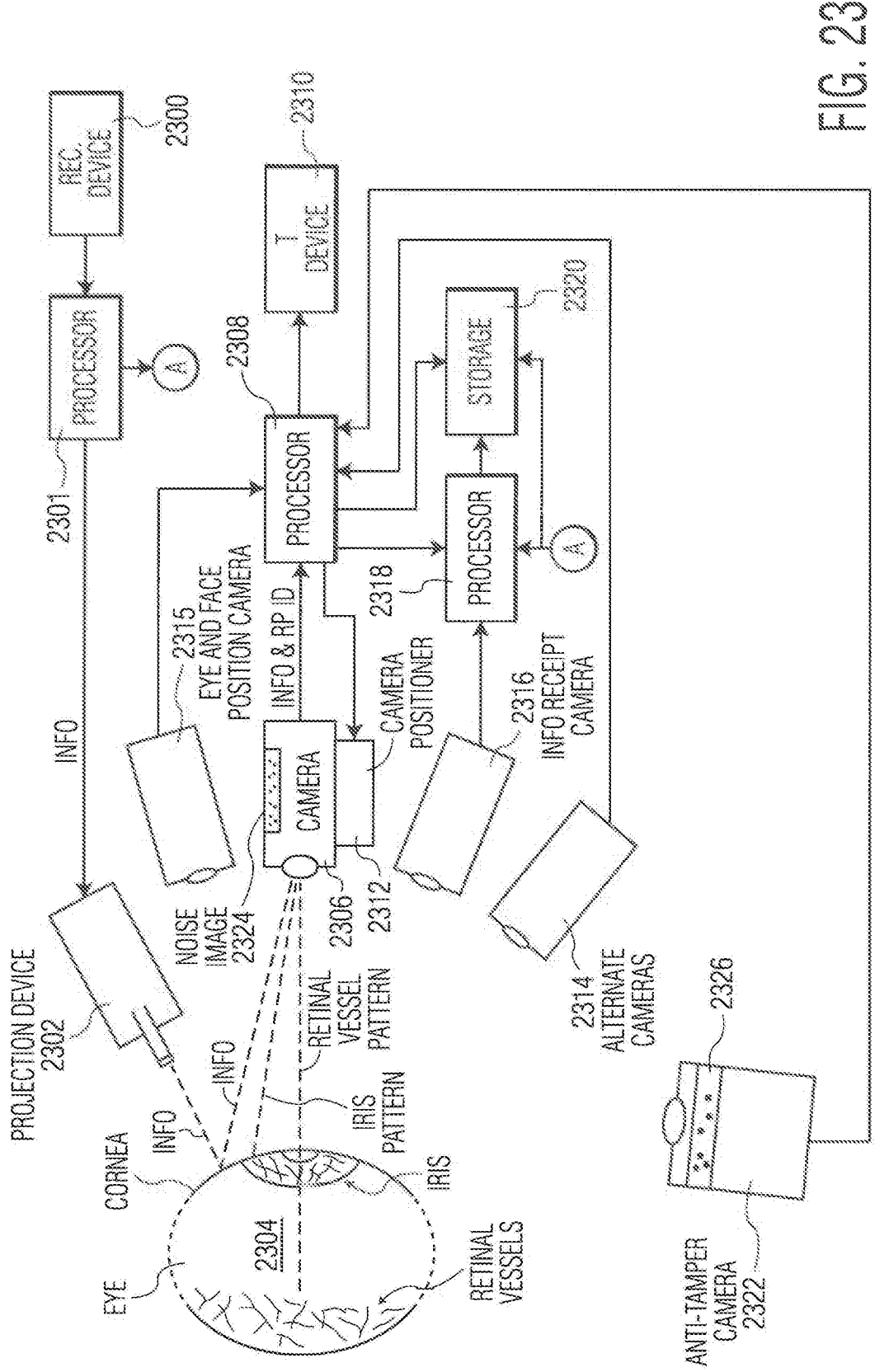
FIG. 23 is another representational diagram of apparatus for projecting information onto an organ comprising an identified biologic feature, and thence to a camera.

FIG. 23 shows a detailed version of this embodiment of the invention. Projection device 2302 receives coded information from receiving device 2300 which is projected onto eye 2304. Camera 2306 images the eye and BI (e.g. retinal vessel pattern or iris pattern) and sends the composite image via processor 2308 and transmitting device 2310 back to the processor which was the source of the code (e.g. 1700 in FIG. 17A) for analysis. Thus the display screen is, effectively, the reflective surface of the eye. In order to deal with the fact that making such an arrangement functional requires that the eye be positioned so that the reflected image falls on the imaging device of camera 2306, various enhancements include:
- (a) camera positioner 2312, which receives positioning signals from processor 2308. Camera 2316, which views eye and face position provides information for 2308, as does the image viewed by 2306;
- (b) the addition of alternate cameras, such as camera 2314, which serve the same function as camera 2306, but are situated in alternative locations;
- (c) (not shown in the Figure) a positioning device similar to 2312, electrically linked to processor 2308 and mechanically linked to projection device 2302.

Figure 24:
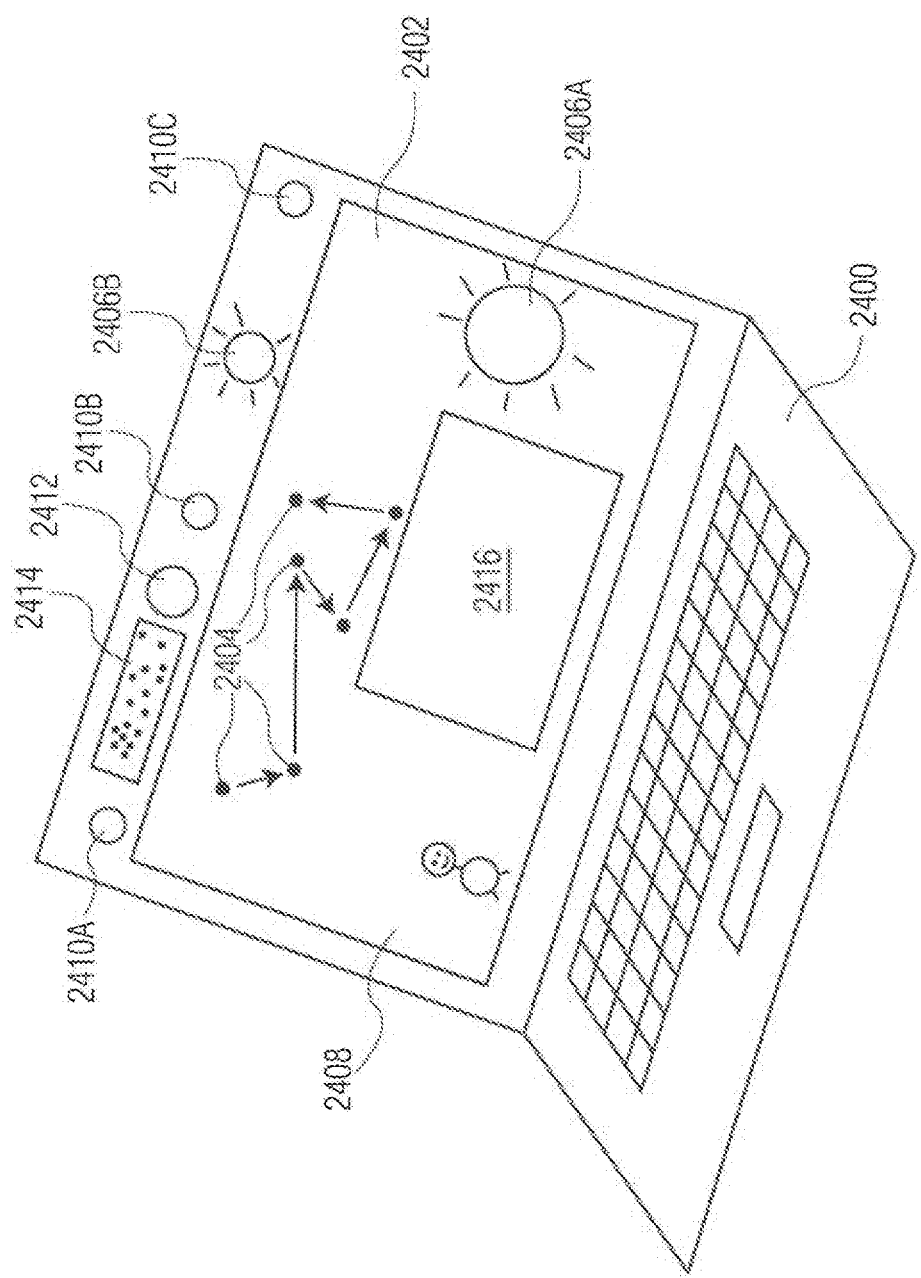
FIG. 24 is a representational diagram of a computational device which performs the functions of both the second and the third preferred embodiments of the invention.

In addition, prompts directed to the RP indicating instructions for orienting the face and eyes will enhance the success of this approach. Once such apparatus is shown in FIG. 24, in which a moving dot on screen 2402 indicates a preferred direction of gaze for the RP. The information for the dot position is supplied by processor 2308 of FIG. 23, and is updated on a high frequency basis. Many other arrangements for stabilization of the geometric arrangement of projection device, RP eye and cameras will be obvious to those skilled in the art.

Referring again to FIG. 23, message transmission in this embodiment of the invention also entails bouncing a light beam off of the eye, for detection by camera 2316 and storage (via processor 2318) in 2320; alternatively the message route could be 2306 to 2308 to 2318 to 2320.

Camera 2322, referred to as an anti-tamper camera is configured to view the one or more of the elements in the Figure to prevent tampering with them. It can also view a screen 2324 on the housing of camera 2306, which displays a code (either the same of a different code as reflected off of the eye), for verifying the identity of camera 2306. Alternatively, or in addition, camera 2306 can view a code on screen 2326 attached to the housing of the anti-tamper camera. The code displayed by 2326 may be the same as either of the aforementioned codes or different.

Referring again to FIG. 24, the laptop is configured to provide many of the features presented hereinabove. These include (a) multiple cameras 2410A-C, a light source for pupil/iris manipulation which is either screen based (2406A) or discrete (2406E), a projection device 2412 analogous to that of FIGS. 22E and 23, and a code display device 2414, for use in conjunction with the mirror apparatus of FIG. 22E. (Alternatively, the mirror device could be utilized with the code displayed on screen 2402. The secure message for a verified RP would be either displayed on 2402, stored in a memory device of 2400, stored in an external memory device, or a combination of these.

Figure 25:
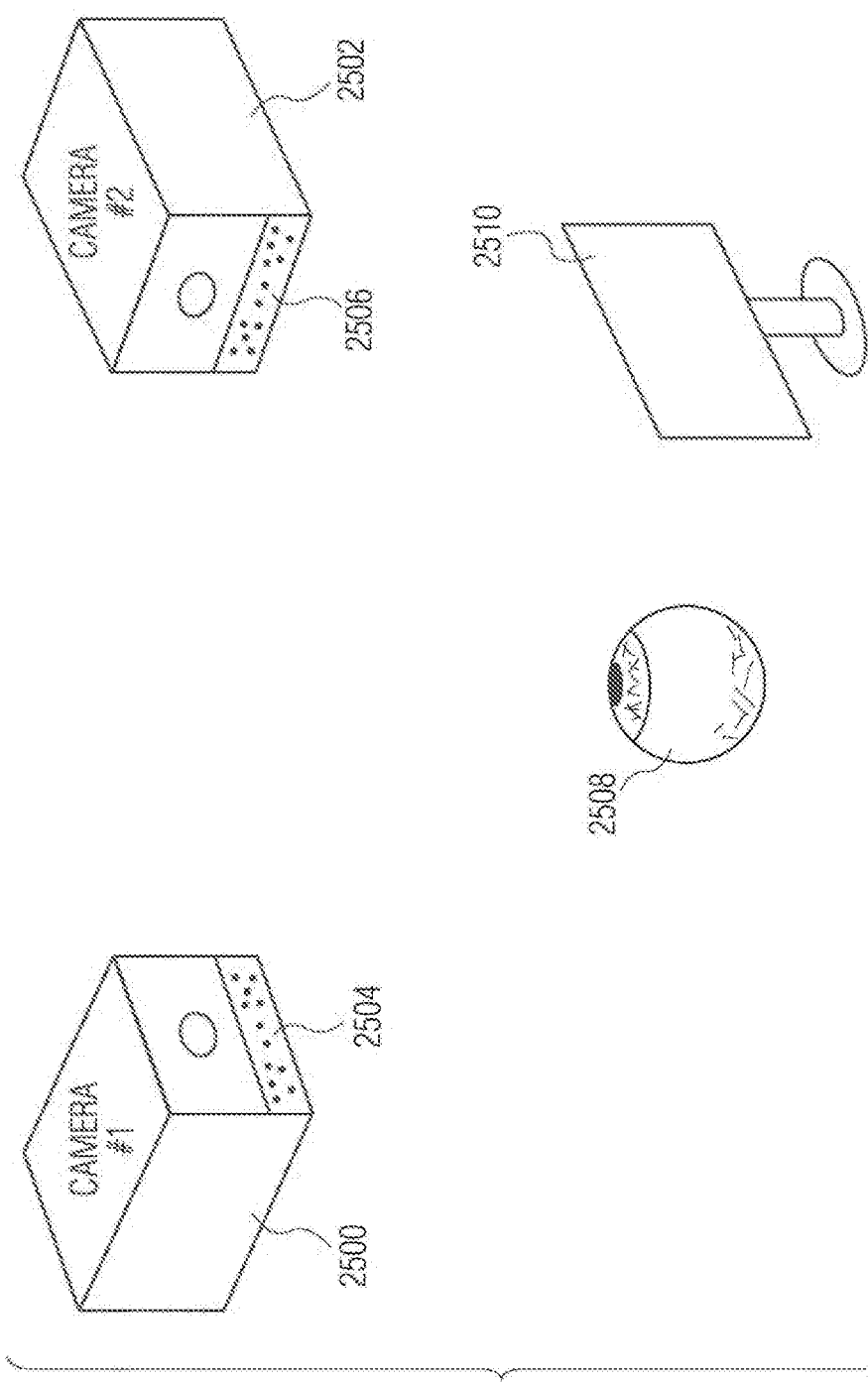
FIG. 25 is a representational diagram of an arrangement of cameras for further enhancing the security of both the second and the third preferred embodiments of the invention.

FIG. 25 shows an embodiment of the multicamera security system, in which each of two cameras 2500 and 2502 observes (a) the other camera and (b) at least one of (i) the bio ID 2508, and (ii) the code display screen 2510. At least one camera also comprises a respective code display screen 2504 and 2506, for verifying the identity of the camera. The code representation displayed by each of 2504, 2506 and 2510 may be the same or different.

The inventions described herein are applicable for preventing an inappropriate person from gaining access to secret or classified information in a remote computer memory. Gaining access includes copying, adding to, deleting from, manipulating and corrupting the information.

Figure 26:
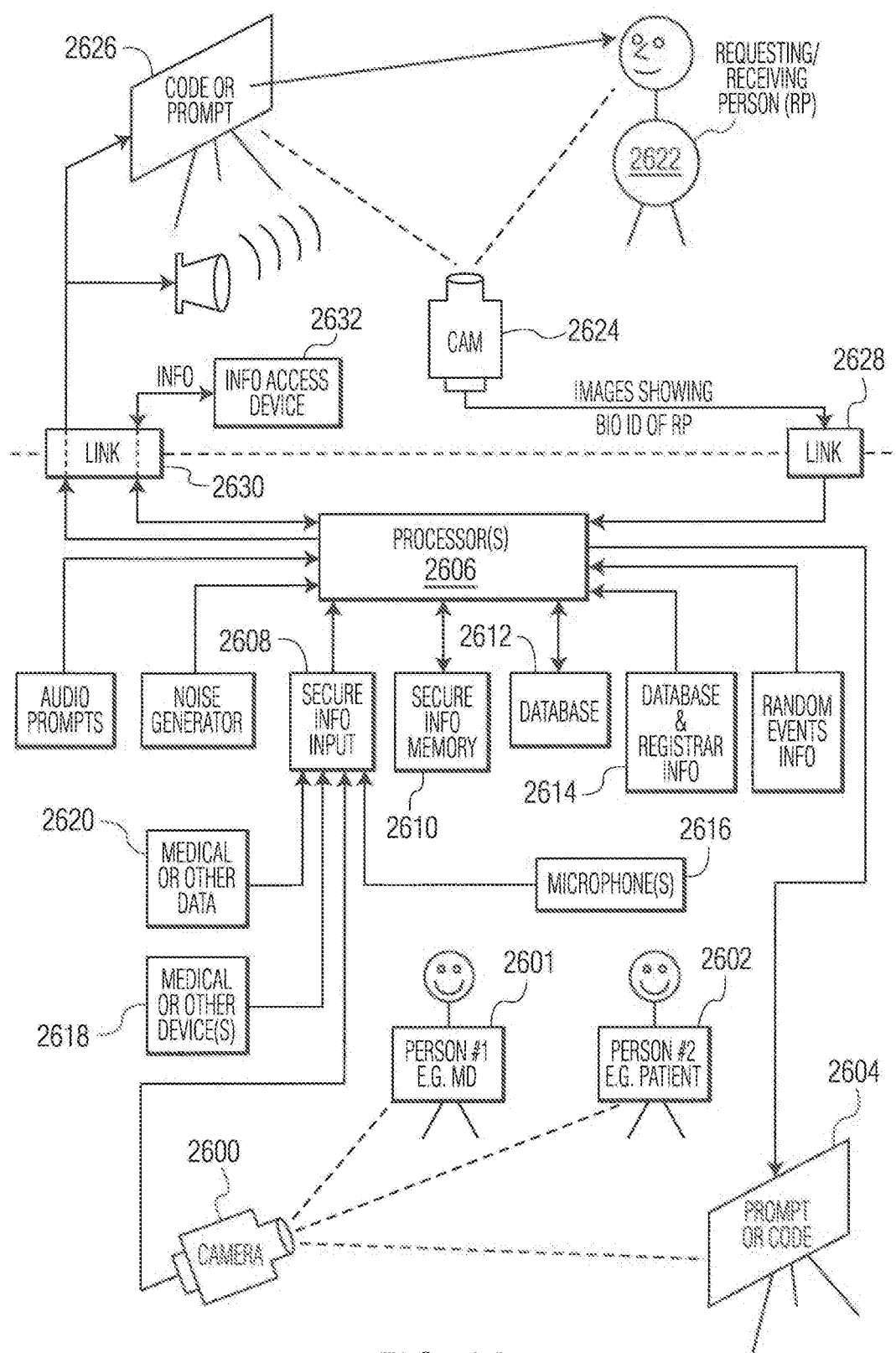
FIG. 26 shows a block diagram of apparatus for providing secure documentation of an encounter between two persons, and for later secure access of the documentation.

FIG. 26 shows apparatus for documenting an encounter between two or more individuals, and later providing secure access of the documented encounter. The encounter may be that between a medical professional (e.g. doctor, nurse, etc.) and a patient, between an attorney and a client, between the participants in a contract, between or among the participants in a business arrangement, a government interaction, etc. For simplification of presentation, the participants in the encounter will hereinbelow be referred to as "Person #1" and "Person #2", and as a group will be referred to as "Persons". The invention provides for the highly reliable identification of these Persons, using biodynamic techniques detailed in U.S. Pat. Nos. 8,233,672, 9,152,837 and 9,563,810, each to Matos. The biodynamic techniques described therein allow not only for the observation of a biologic marker such as an iris pattern, but for manipulation of the marker, by manipulating, for example, the amount of incident light. Such biologic manipulation is referred to herein as the provision of a prompt. The prompt may control the brightness of a light (which may repeatedly or continuously change), a direction of gaze of the person as he/she follows a moving object on a screen, etc., as described hereinabove.

An alternative to enhancing the information contained in the biologic ID is the provision of a complex pattern of information on a screen, near enough to the person to be identified that a single camera can visualize both the screen and the Persons.

In the Figure, camera 2600 visualizes each of Person #1/element #2601, Person #2/element #2602, and may image prompt or code screen 2604 if the display of code is utilized for biologic identification enhancement. The code or prompt manipulation is controlled by system processor(s) 2606. Information concerning the medical encounter is inputted to memory 2610 by processor 2606. The identity of Person #1 and Person #2 is stored in database 2612, having been inputted to the database by a registration person utilizing input apparatus 2614.

The camera may visualize the iris, retinal blood vessels, veins of the hand, a fingerprint, a face. It may visualize veins in other parts of the body. It may visualize arteries. In the case of the iris the response to light of circular muscle fibers and radiating muscle fibers of the iris will modulate the iris pattern. A voluntary change in focus (which may occur as a result of a prompt requesting this) will also produce a change in the size of the iris. For visualized retinal vessels, the change in pupil size caused by iris manipulation will affect the size of the viewable vessel field. The movement of other parts of the body containing biologic identifiers in response to a request will provide a dynamic aspect to the identification. Screen 2604 is intended to also indicate a speaker for providing such audio instruction.

Microphone 2616 serves the dual purpose of (i) providing an audio record of the encounter, and (ii) providing a voiceprint of each participant.

If the encounter is a medical one, then information from medical instruments and equipment 2618 used in an examination (such as a stethoscope or an ECG machine) are inputted. Pertinent text and other data are inputted via 2620.

The aforementioned setup is applicable in all phases of medical encounter including a doctor's office consultation room, a doctor's office examining room, an operating room, a hospital room, etc.

In the case of a non-medical encounter, each of the elements in the Figure is applicable except for 2618.

The upper part of the Figure shows the mechanism by which a person 2622 (i) requesting access to information about the encounter may gain such access, and (ii) requesting to enter information in conjunction with the encounter may do so. Camera 2624 images both 2622 and screen 2626 if code is used for identification enhancement.

The image information is conveyed to 2606 via link 2628. The link may be a direct/hard-wired connection, a radiofrequency connection, an Internet connection, a fiber-optic cable connection, private network connection or other means of broadband linkage. Another link 2630 allows (i) the conveyance of prompts or code to 2626, and (ii) the conveyance of access of person 2622 to secure information memory 2610 via processor 2606 and information access device 2632. Link 2630 may comprise any of the means recited in conjunction with link 2628; the 2630 means need not be the same type as the 2628 means. Furthermore, the information access component of the link need not be the same as the prompt/code conveying component.

When the biologic identifier enhancement technique involves a code containing screen, techniques for synchronizing screen 2626 changes and camera 2624 image acquisition may be utilized, as are known in the art, and may be performed by processor 2606 or another processor.

As indicated in conjunction with the receiver identification technology which is the subject of U.S. Pat. Nos. 9,152,837 and 9,563,810 to Matos, audio instructions may serve as prompts, and noise and other codified random events or pseudorandom events may serve as a basis for code.

A broken line in the Figure indicates a possible separation of the access requesting person, who may be at the scene of the secure memory 2610, or remote from it.

Figure 27:
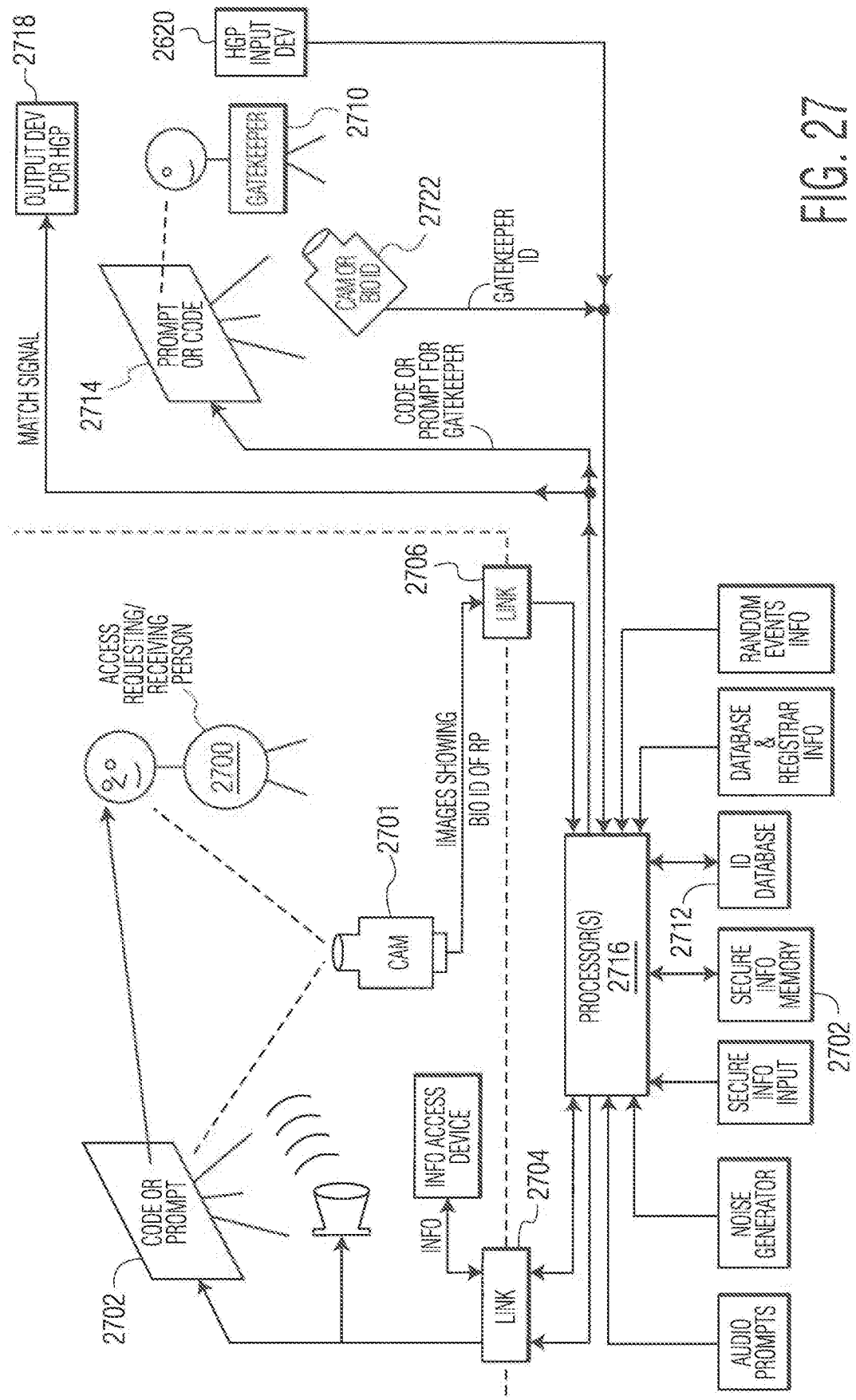
FIG. 27 shows a block diagram of apparatus for providing secure access to information contained in a computer memory.

FIG. 27 shows another embodiment of the invention for enhancing the security of a receiver identification system, i.e. a system in which an access requesting person 2700 requests access to a digital memory 2702, to either copy, add, delete or manipulate data in the memory. The core of the system is similar to that shown in FIGS. 16A to 17C herein, and discussed in the corresponding sections of the specification. In a generalization of the aforementioned six FIGS. 16A through 17C, screen 2702, a biologic identification output device, provides either (i) one or more prompts, or (ii) changing code. Links 2704 and 2706, as described in similar fashion to above-mentioned 2630 and 2628 may represent a direct connection (as in the case of FIGS. 16A and 17A), a radiofrequency link (as in the case of FIGS. 16B and 17B), or any other type of communication network (as in the case of FIGS. 16C and 17C); non-identical 2704 type and 2706 type are possible.

When the biologic identifier enhancement technique involves a code containing screen, techniques for synchronizing screen 2702 changes and camera 2701 image acquisition may be utilized, as are known in the art, and may be performed by processor 2606 or another processor.

In addition, a gatekeeper or gatekeeping person, HGP, observes the analysis of a comparison of (i) the inputted biodynamic (i.e. manipulated by prompt and or code-containing screen 2702) identification information of 2700 with (ii) the corresponding biologic information of the person that 2700 claims to be. If the person that 2700 claims to be is authorized to use the system, then their biologic identification information will be stored in 2712. Processor 2716 performs this comparison, and reports the results to 2710 via output device 2718. A match signal sent to 2718 may indicate a simple binary result (i.e. "yes" or "no"), a numerical value of goodness of fit, or a multidimensional analysis of goodness of fit. It may include a request for more information such as a specific suggestion for prompt manipulation. Based on the 2718 output, the HGP inputs a response to 2620, which may be to accept the request for information by 2700, to deny the request or to continue with a further identification analysis.

The human may be expected to have certain advantages useful for a final "yes" or "no" decision, that may relate to factors other than just the identification, including, patterns of information request(s) over time, the nature of a particular request, current events related to information system breaches, other current events and the like. Furthermore, the human gatekeeper may prefer to analyze the biologic information himself/herself, and may not necessarily agree with the outputted analysis of processor 2716.

In another embodiment of the invention, access of 2700 to memory 2702 is provided only if both (i) the analysis of processor 2716, and (ii) the HGP analysis are in agreement to provide access. In this case, the human gatekeeper cannot overrule the processor analysis result.

Since the enhancement of security by adding a gatekeeper depends on having the gatekeeper be the person that he/she claims to be, gatekeeper identification is desirable. There are various possible levels of such HGP identification. In FIG. 27, camera 2722 (or other biologic ID device) provides HGP biologic identification information to processor 2716. If there is no match, then the gatekeeper cannot access the system, in which case 2700 cannot access the system. In a preferred embodiment of the invention, the gatekeeper is subject to the process of biodynamic identification, such that a biologic feature of the HGP is manipulated by prompts or enhanced by visualized code, each provided by biologic output device 2714 (which shown as a screen but it need not be; For instance, it could be a light source which causes changes in the state of contraction and relaxation of the muscles of the iris.)

As discussed hereinbelow in conjunction with FIG. 32B, still more complex gatekeeper identification systems are possible. Furthermore, systems with a plurality of gatekeepers are possible; for highly sensitive information or information of great importance, the agreement of multiple gatekeepers may be required, each set up with one of the aforementioned types of gatekeeper identification. Numerous variations are possible including:

HGP input is sought only when the analysis of the identification match of 2700 with stored memory images in 2712 by processor 2716 yields an intermediate value. For high levels of match or non-match, the processor may act autonomously;

Arrays of multiple HGPs may include hierarchies where a high level gatekeeper person monitors the activity of one or more lower level gatekeeper persons;

Still more complex arrays of monitoring may include one or more processors which monitor the decision making of one or more gatekeepers—i.e. these processors carry a higher level of decision making weight than the gatekeeper; and Still other complex arrays involve a plurality of identification information analyzers (persons or gatekeepers) wherein a decision may be made by a majority vote, a ⅔ or more vote, etc.

A dotted line in the Figure indicates a possible separation of the access requesting person, who may be at the scene of the secure memory 2702, or remote from it. The gatekeeper is shown in proximity to the processor and memory, which would be expected to increase information security; however, invention configurations with the HGP not near the secure memory are possible as well.

Figure 28:
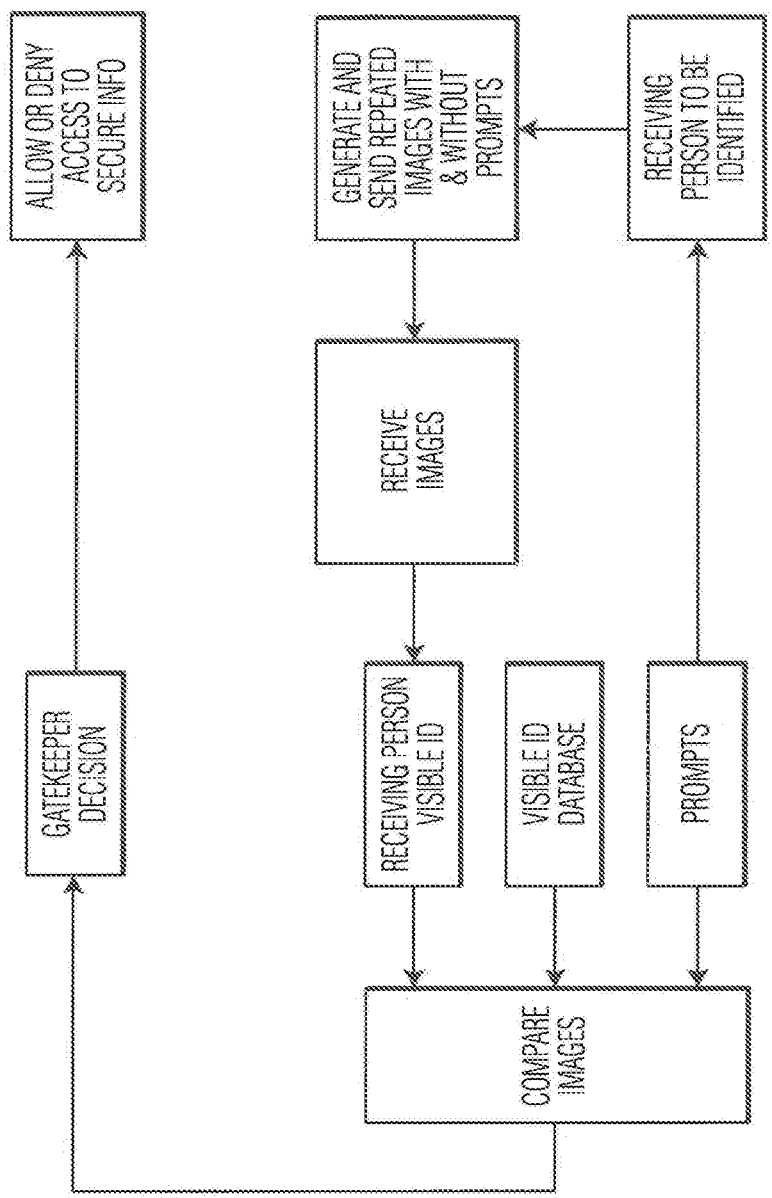
FIG. 28 shows a block diagram showing the operation of the apparatus in FIG. 27.

FIG. 28, analogous to FIG. 18 of the parent application, shows a block diagram of system events in which prompts (e.g. light source manipulated by processor [the processor controls access to the secure information] controls the iris musculature) are utilized to enhance a biologic identifier. The aforementioned various possible control-sharing relationships between the processor(s) and the gatekeeper(s) are possible.

Figure 29:
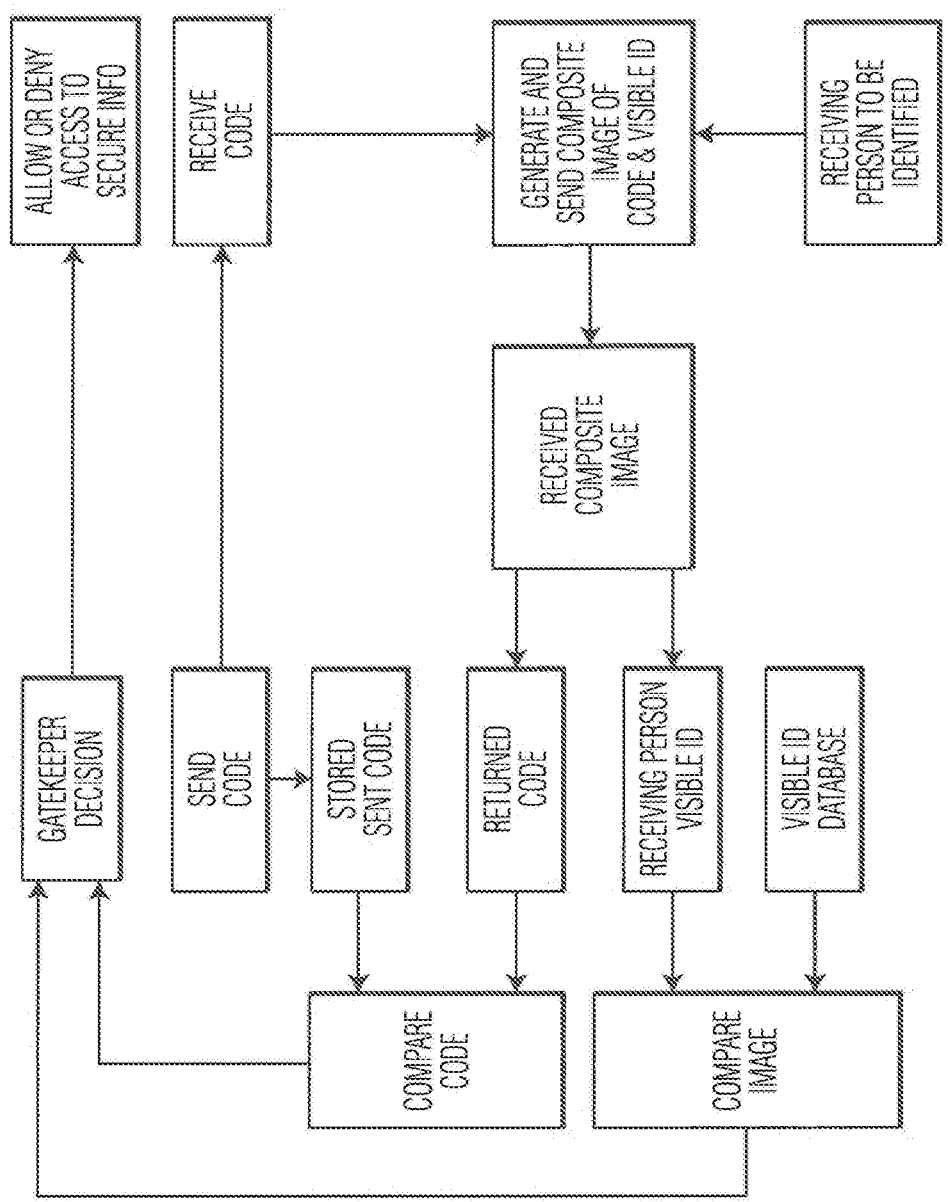
FIG. 29 shows another block diagram showing the operation of the apparatus in FIG. 27.

FIG. 29, analogous to FIG. 19 of the parent application, shows a block diagram of system events in which code manipulated by the processor [the processor controls access to the secure information]) is utilized to enhance a biologic identifier. The aforementioned various possible control-sharing relationships between the processor(s) and the gatekeeper(s) are possible.

Figure 30A:
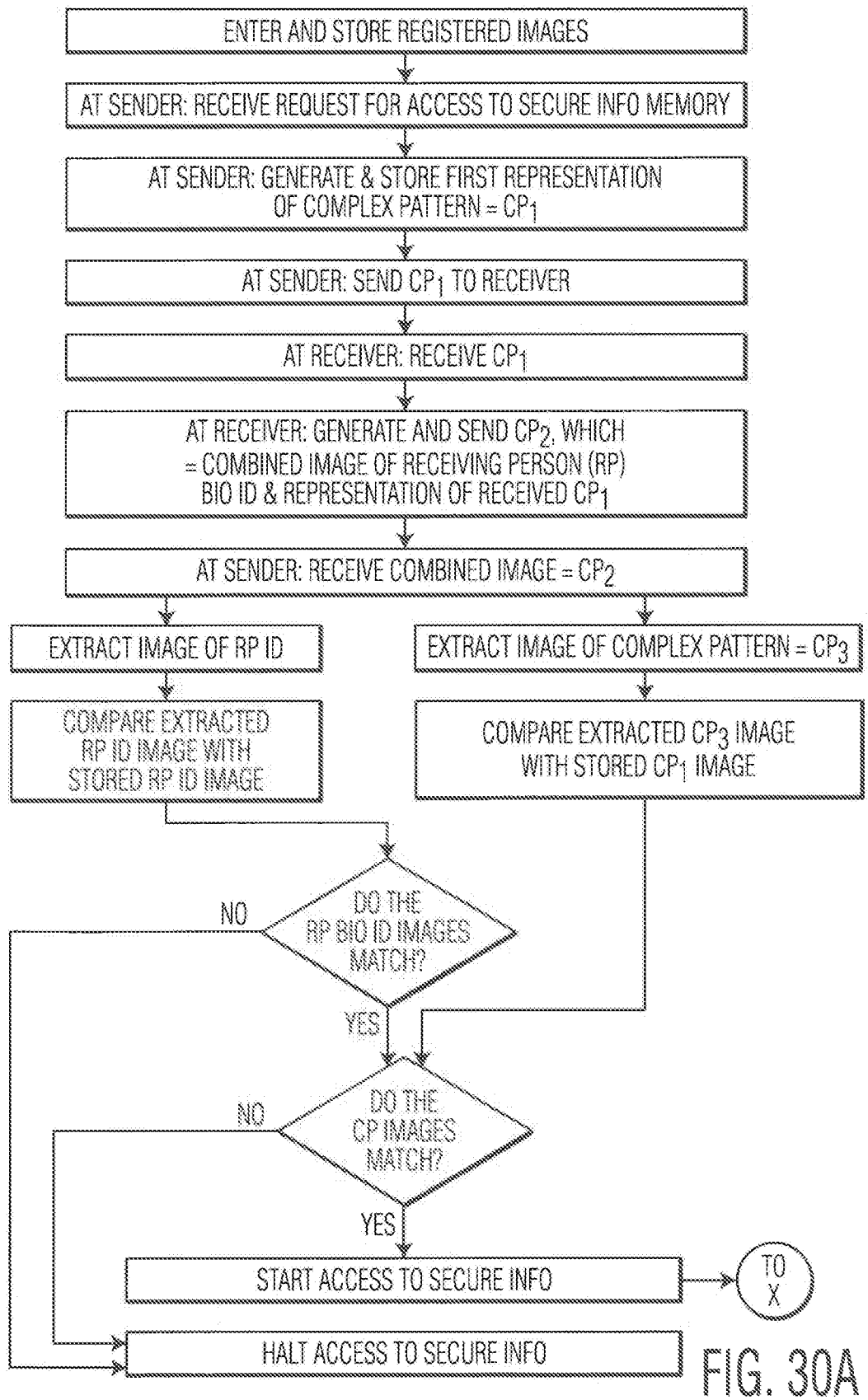
FIGS. 30A and 30B, together are a flow diagram showing one type of operation of the apparatus in FIGS. 26 and 27.
Figure 30B:
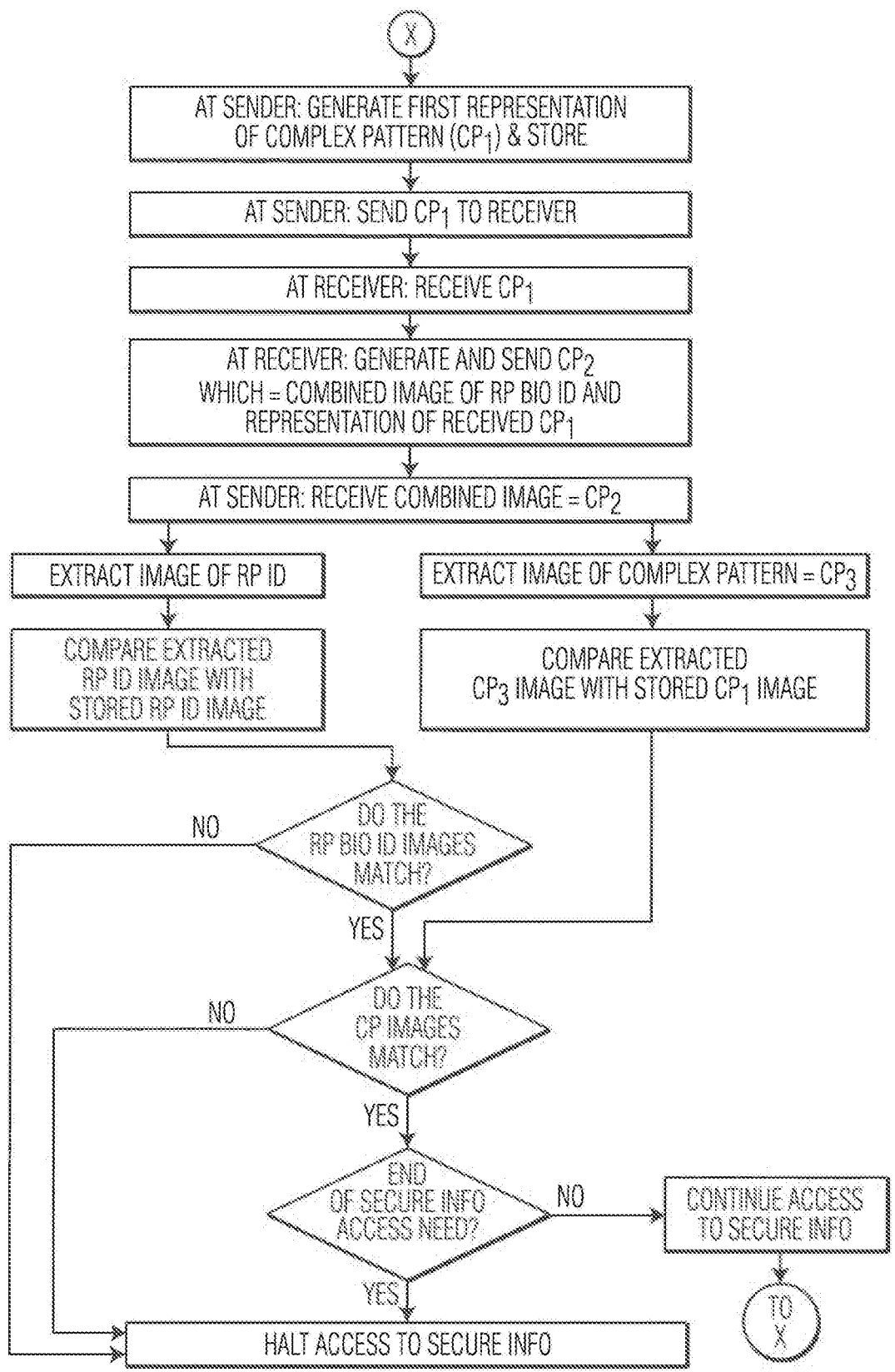

FIGS. 30A and 30B are analogous to FIGS. 21A and 21B of the parent application. A somewhat different nomenclature is utilized in FIGS. 30A and 30B (compared to FIGS. 21A and 21B. In 30A and 30B, three types of code representation are defined:

(1) a first representation, which specifies the exact coded information;

(2) a second representation, which is the combined image of the biologic identifier and the code; and (3) a third representation, which is the extracted image of the code, after it has been separated from the returned composite image.

The third representation is compared with the first representation in the determination of authenticity of the composite image. The distortion implicit in imaging techniques will prevent a perfect match of the first and the third representation. But even lesser degrees of match are expected to be very difficult for a hacker or unauthorized attempting user to duplicate.

In conjunction with FIGS. 21A and 21B, there were only two representations, which correspond to the first and the third representations referred to in FIGS. 30A and 30B.

Analyses with larger numbers of representations are possible; each such scheme recognizes the concept that (i) there are many steps along the "round trip" that the code makes from the processor to the remote access requester and back, and that (ii) the code may suffer some degree of distortion/degradation as it makes each such step.

Figure 31:
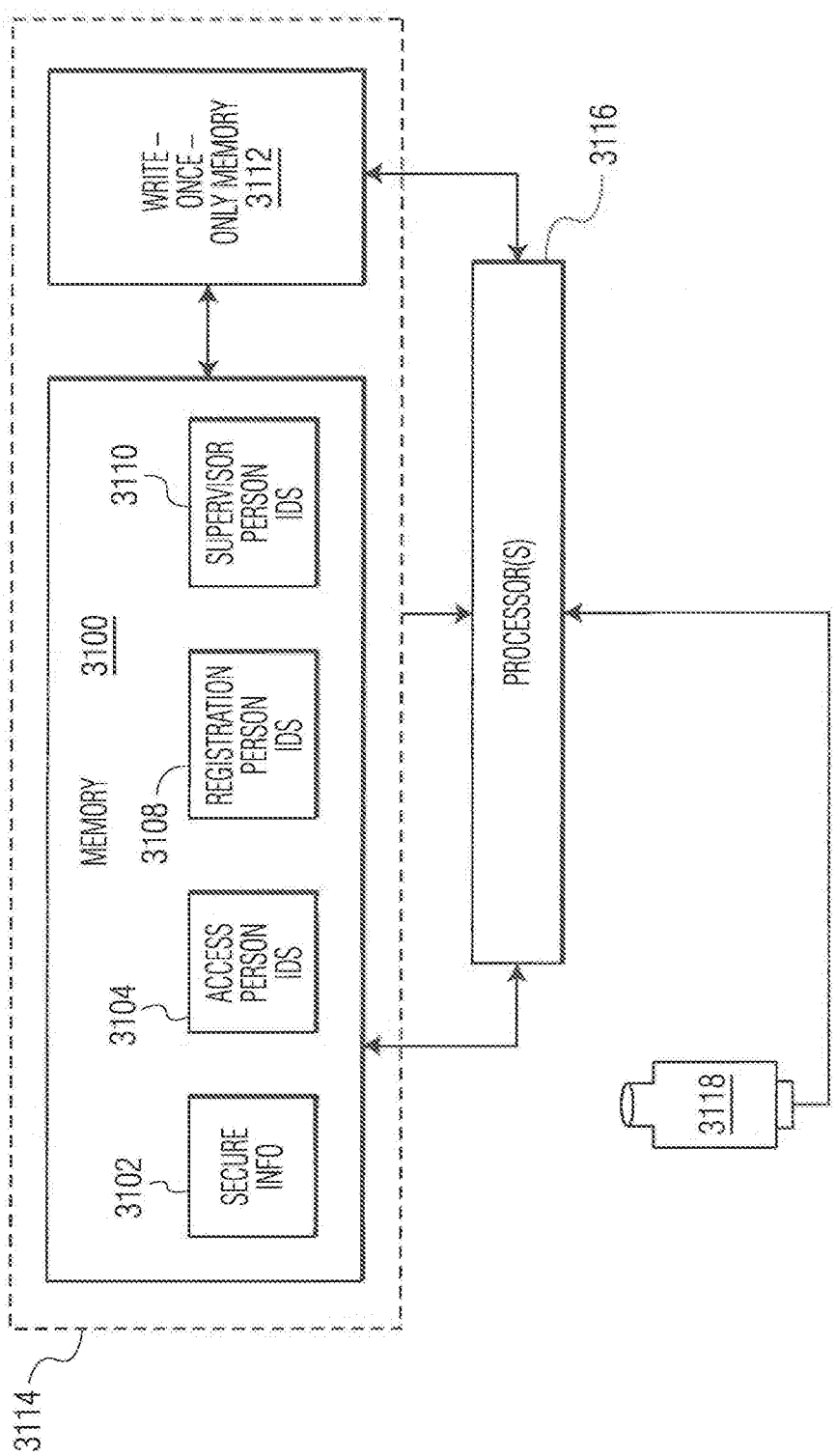
FIG. 31 shows a block diagram of a computer memory with representations of information stored therein.

FIG. 31 shows a schematic of the storage of secure information 3102 as well as the identifying information of a number of possible key individuals in memory 3100. The identification information of these individuals will include biologic data (e.g. iris images under a plurality of lighting conditions/pupil sizes), and in most cases will also include alphanumeric information indicating a name or identifying number or other indicating data. 3104 comprises the identification of individuals allowed to access data.

3106 comprises identification information of registration persons; In order for there to be secure entry of biologic identification information of access persons to be newly entered into memory as acceptable users, biologically identifiable registration persons, known to pass security muster, must be allowed to access the system.

3110, the identification information of supervisory personnel is intended to indicate one step up in the hierarchy of trusted individuals; The supervisory personnel are persons allowed to register registration persons. Some supervisory personnel may be allowed to enter the identification information of other supervisory personnel. Some registration personnel may be allowed to enter the identification information of other registration personnel. Some supervisory personnel may be allowed to enter the identification information of other accessing persons. Systems with fewer or greater numbers of levels of hierarchy are possible.

After manufacture of the system, there must be at least one person who is allowed access. This can be accomplished with a similar hierarchical setup in the manufacturing facility. It can also be accomplished by allowing the first person who uses the system to enter his/her own identification information without the permission/approval of another person. It can also be accomplished by having at least one person's identification information inserted in a write-once-only memory 3112 at the time of production.

Systems are possible with one memory or more than one memory. Systems are possible without a write-once-only memory or with more than one write-once-only memories. The memory may reside in a microprocessor, microcontroller, a hard drive, or other digital information repository, as is known in the art. The write-once-only memory may be PROM-based, EPROM-based, EEPROM-based or use other non-labile configurations as are known in the art.

The memory may be protected by tamper-detecting seal(s) 3114 (shown as a broken line in the Figure; the broken line is not intended to specify a construction feature of such seals, which are known in the art). The seals communicate with a processor 3116. In the Figure this is the processor which provides information for the memory and retrieves information from it. There may be more than one processor involved in management of memory information. Seal information may be managed by the same processor(s) as used in user identifying information management or another processor. A camera 3118 may constantly observe the memory to enhance security, relaying information to either 3116 or another processor.

Figure 32A:
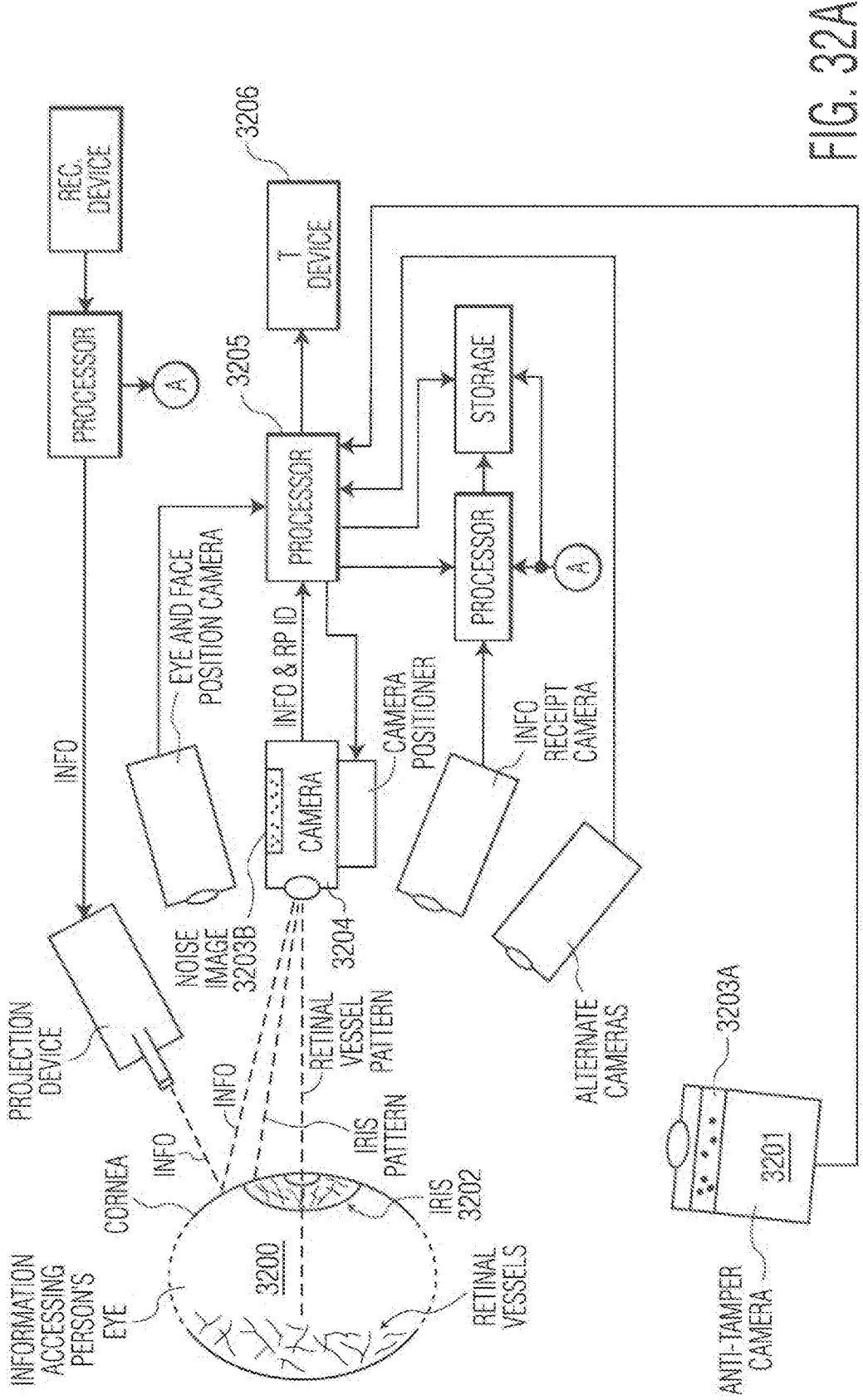
FIG. 32A shows a representational diagram of apparatus for projecting information onto an organ comprising an identifiable biologic feature of an information accessing person, and thence to a camera.
Figure 32B:
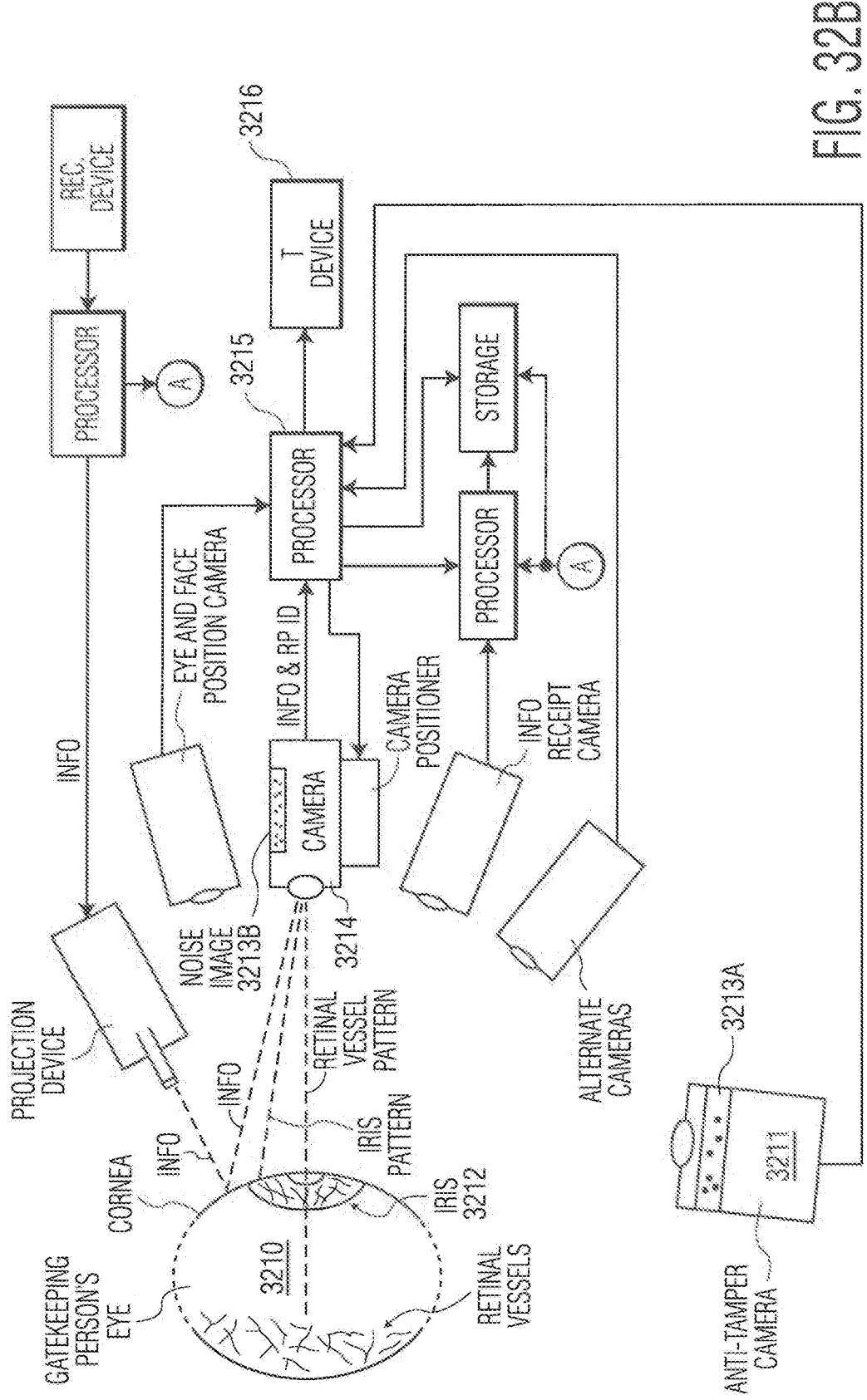
FIG. 32B shows a representational diagram of apparatus for projecting information onto an organ comprising an identifiable biologic feature of a gatekeeping person, and thence to a camera.

FIGS. 32A and 32B show a technique for further enhancing the security of information transmission by using the technique in the Figure for identification of each of:

(i) a person desiring to gain access to a computer memory (FIG. 32A), and (ii) a gatekeeping person (FIG. 32B), as described hereinabove, who receives information about persons wishing to access a computer memory; Such information may itself constitute secure information and therefore require ongoing identification of the gatekeeping person.

These figures show an information path to the receiving person which traverses the reflective surface of the eye (3200 for the information accessing person/FIG. 32A, and 3210 for the gatekeeping person/FIG. 32B), and does so in close proximity to the biologic identifier, the respective irises 3202 and 3212. Since respective cameras 3204 (FIG. 32A) and 3214 (FIG. 32B), return a composite image of both (i) the respective irises and (ii) the sent information to the sender via respective processors 3205 (FIG. 32A) and 3215 (FIG. 32B), and respective transmitting devices 3206 (FIG. 32A) and 3216 (FIG. 32B), the sender is able to determine the identity of the receiver with a high degree of certainty. Further enhancements to the security of the system are the respective anti-tamper cameras (3201 and 3211), the noise images (3203A/B and 3213A/B), and the ability to supply visual prompts which manipulate the iris itself.

There has thus been shown and described a novel system for verifying the identity of an author and for verifying the identity of a person receiving information or using a computer system, which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Apparatus for controlling the access of a particular human individual to a computer memory for a given period of time by repeatedly assessing a changeable visible identifying feature ("VIF") of said human individual, and by assessing an identifying feature of a gatekeeping human individual said apparatus comprising, in combination:
   (a) a computer memory operative to store and provide (i) secure information, (ii) information representing a plurality of images of a VIF pertaining to at least one registered accessing human individual ("RAHI") authorized to access said secure information and (iii) information representing a plurality of images of a VIF pertaining to at least one registered gatekeeping human individual ("RGHI") authorized to enable access to said secure information;
   (b) a first processor coupled to the memory, operative to store selected information in the memory and to access selected information from the memory, and operative to produce (i) a plurality of first supplementing signals, (ii) at least one second supplementing signal, and (iii) a plurality of assessment signals;
   (c) a first camera, coupled to said first processor,
      (1) arranged to capture images of a visible identifying feature of a putative accessing human individual ("PAHI"), and
      (2) configured to repeatedly generate successive test images of said VIF of said PAHI during a given period of time for transmission to said first processor;
   (d) a first supplemental identification device ("SID"), arranged in the vicinity of said first camera, coupled to said first processor, and configured to supplement the test image information provided by said first camera in response to said at least one first supplementing signal received from said first processor, said first SID producing at least one of:
   an output configured to induce a change in the appearance of said VIF of said PAHI; and
   an output configured and arranged to display a visual representation of information represented by said first supplementing signal, wherein said first camera is arranged to capture images showing both said visual representation and a VIF of said PAHI, wherein said first SID modifies at least some of the visual information captured by said first camera;
   (e) a second camera, coupled to said first processor, arranged to input VIF information pertaining to putative gatekeeping human individual ("PGHI");
   (f) a second SID, arranged in the vicinity of said second camera, coupled to said first processor, and configured to supplement the information provided by said first camera in response to said at least one second supplementing signal received from said first processor, said second SID producing at least one of:
   an output configured to induce a change in the appearance of said VIF of said PGHI; and
   an output configured and arranged to display a visual representation of information represented by said second supplementing signal, wherein said second camera is arranged to capture images showing both said visual representation and a VIF of said PGHI, wherein said second SID modifies at least some of the visual information captured by said second camera;
   (g) an output device, coupled to said first processor, operative to provide match information represented by said assessment signals to said RGHI; and
   (h) an input device, coupled to said first processor, operative to provide a signal to said processor representing an inputted access command from said RGHI pertaining to granting access to said memory, to a PAHI;
wherein said first processor is operative to:
   (1) repeatedly generate said first supplementing signal for transmission to said first SID;
   (2) repeatedly compare each of said successive test images of said VIF of said PAHI received from said first camera, with said stored images of the VIF of said at least one RAHI to repeatedly assess the identity of the PAHI during said given period of time; and generate said at least one assessment signal indicating at least one result of said repeated assessment of the identity of the PAHI;
   (3) assess the inputted identification information of said PGHI to determine whether or not the PGHI is an RGHI, in dependence on whether or not the information contained in the inputted identification information of the PGHI matches the stored identification information of the RGHI;
   (4) provide the result of said repeated assessment to the output device; and
   (5) allow access by the PAHI to said memory for a given period of time, following the input of an access command by said RGHI.

2. The apparatus defined in claim 1, wherein said first processor is operative to allow reading of said secure information in said memory by said PAHI in response to receipt of a first command signal and wherein said input device is further operative to provide said first command signal in response to a respective PGHI input.

3. The apparatus defined in claim 1, wherein said first processor is operative to allow storage of said secure information in said memory by said PAHI in response to receipt of a second command signal and wherein said input device is further operative to provide said second command signal in response to a respective PGHI input.

4. The apparatus defined in claim 1, wherein said given period of time is selected from the group consisting of:
   (a) less than 1 minute;
   (b) 1 to 5 minutes;
   (c) 5 to 15 minutes; and
   (d) more than 15 minutes.

5. The apparatus defined in claim 1, wherein said first processor is operative to prevent PAHI access to said memory upon an assessment, by said first processor of a non-match between the inputted test image of said PAHI and the stored images of said RAHI.

6. The apparatus defined in claim 1, wherein said at least one assessment signal indicates a degree of match of the test image of said PAHI with the stored images of said RAHI.

7. The apparatus defined in claim 6, wherein said first processor is operative to prevent PAHI access to said memory upon a determination by said first processor of a degree of match less than a first given number, wherein said degree of match less than said first given number indicates a high likelihood of a non-match of the test image of said PAHI with the stored images of said RAHI.

8. The apparatus defined in claim 6, wherein said first processor is operative to allow PAHI access to said memory upon a determination by said first processor of a degree of match greater than a second given number, wherein said degree of match greater than said second given number indicates a high likelihood of a match of the test image of said PAHI with the stored images of said RAHI.

9. The apparatus defined in claim 1, wherein each of said first camera, said first SID, said first processor, said computer memory, said second camera, said second SID, said output device and said input device is situated at a common location.

10. The apparatus defined in claim 1, wherein said first camera and said first SID are situated at a remote location from said computer memory, said first processor, said second camera, said second SID, said output device and said input device, and wherein said apparatus further comprises:
(a) a first transmitting and receiving ("T/R") device, coupled to said first processor, for transmitting said at least one first supplementing signal to said first SID and for receiving said successive test images from said first camera;
(b) a second T/R device, for communication with said first T/R device, coupled to each of
(1) said first SID for receiving said at least one first supplementing signal, and
(2) said first camera, for transmitting said successive test images;
wherein
(a) said first processor is further operative to cause said first T/R device to transmit said at least one first supplementing signal, and to process said received test images;
(b) said first processor, said computer memory, said second camera, said second SID, said output device and said input device are situated at a first location; and
(c) said first camera, and said first SID are situated at a second location, remote from said first location.

11. The apparatus defined in claim 1, further comprising:
(a) a second processor, coupled to each of said first camera and said first SID; and
(b) a communication system, coupled to each of said first processor and said second processor, for exchanging of signals between said first and said second processors;
wherein
(i) said second processor is operative to transmit said successive test images to said first processor via said communication system;
(ii) said first processor is operative to transmit said first supplementing signal to said first SID via said communication system and said second processor;
(iii) said first processor, said computer memory, said second camera, said second SID, said output device and said input device are situated at a first location; and
(iv) said second processor, said first camera and said first SID are situated at a second location, remote from said first location.

12. The apparatus defined in claim 1, wherein said RAHI VIF is at least one pattern of an iris of an eye of the RAHI and wherein said PAHI VIF is at least one pattern of an iris of an eye of the PAHI.

13. The apparatus defined in claim 1, wherein said RAHI VIF is at least one pattern of retinal veins of an eye of the RAHI and wherein said PAHI VIF is at least one pattern of retinal veins of an eye of the PAHI.

14. The apparatus defined in claim 1, wherein said RAHI VIF is a facial pattern of the RAHI and wherein said PAHI VIF is a facial pattern of the PAHI.

15. The apparatus defined in claim 1, wherein said RAHI VIF is selected from the group consisting of a fingerprint and a palm print of the RAHI, and wherein said PAHI VIF is selected from the respective member of the group consisting of a fingerprint and a palm print of the PAHI.

16. The apparatus defined in claim 1, wherein said RAHI VIF is a pattern of veins of a hand of the RAHI and wherein said PAHI VIF is a pattern of veins of a hand of the PAHI.

17. The apparatus defined in claim 1, wherein:
(a) each of said first supplementing signal is a first prompt producing signal;
(b) said first SID is a first prompt producing device, for producing at least one first prompt in response to said first prompt producing signal; and
(c) said first prompt causes a change in the appearance of said VIF of said PAHI.

18. The apparatus defined in claim 17, wherein:
(i) said RAHI VIF is a pattern of an iris of an eye of the RAHI and said PAHI VIF is a pattern of an iris of an eye of the PAHI;
(ii) said computer memory is further operative to store information representing a plurality of images of an iris of an eye of said RAHI, each image captured under different lighting conditions for said iris; and
(iii) said prompt producing device is a light source configured to generate light in response to said at least one first prompt signal, which impinges on said PAHI iris thereby to alter an opening size of said PAHI iris;
wherein said first processor is further operative to change said lighting conditions by generating said at least one first prompt signal;
wherein said first processor is further operative to compare information representing a plurality of viewed images of said PAHI iris, each captured under different lighting conditions, with said information representing a plurality of stored RAHI iris images.

19. The apparatus defined in claim 1, wherein said first SID comprises a display device located in proximity to said PAHI for displaying a representation of said first supplementing signal received from said first processor.

20. The apparatus defined in claim 19, wherein the information represented by said first supplementing signal causes said display device to produce a first prompt arranged to induce an alteration in at least one of:
(a) the quantity of light impinging on an eye of said PAHI;
(b) the focus of an eye of said PAHI;
(c) a direction of gaze of an eye of said PAHI; and
(d) an angle of orientation of a face of said PAHI with respect to said first camera.

21. The apparatus defined in claim 19, wherein
(a) said first processor is further operative to generate a first representation of a first information set, and to cause:
(i) said first representation to be stored in said computer memory, and
(ii) said first supplementing signal to specify said first representation;
(b) in response to receipt of said first supplementing signal, said display device is adapted to produce a visual second representation of said first information set; and
(c) said at least one first camera is arranged to image both
(1) said visible identifying feature of said PAHI, and (2) said display device displaying said visual second representation of said first information set, for generating a composite image containing both said identifying feature of said PAHI and said visual second representation of said information set, for transmission to said first processor;

wherein said first processor is further operative to:
  (i) receive said composite image and generate both
    (A) a third representation of said first information set, and
    (B) a representation of said VIF of said PAHI,
  each from the received composite image;
  (ii) compare information contained in said stored first representation of said first information set, with information contained in said received third representation of said information set; and
  (iii) compare information contained in said stored RAHI VIF with information contained in said representation of said VIF of said PAHI; and wherein said at least one assessment signal provides an indication of a result of:
  (A) said first information set comparison and
  (B) said VIF comparison.

22. The apparatus defined in claim 21, wherein said at least one assessment signal provides information indicating a degree of match of said first information set comparison.

23. The apparatus defined in claim 1, wherein said first SID comprises a display device located in proximity to said PAHI, and wherein said apparatus further comprises a communication link between said first processor and said display device, wherein said communication link is selected from the group consisting of (a) a wired link, and (b) a wireless link.

24. The apparatus defined in claim 1 wherein said second camera is adapted to input at least one of:
  (a) at least one pattern of an iris of an eye of said PGHI;
  (b) at least one pattern of retinal veins of said PGHI;
  (c) an image of a face of said PGHI;
  (d) a VIF selected from the group consisting of a fingerprint and a palm print of said PGHI; and
  (e) a pattern of veins of a hand of said PGHI.

25. The apparatus defined in claim 1, wherein said first processor is operative to repeatedly assess said PGHI VIF information, and to prevent PAHI access to said memory upon an assessment, by said first processor of a non-match between the inputted VIF information pertaining to said PGHI and the stored VIF information pertaining to said RGHI.

26. The apparatus defined in claim 1,
  wherein said first processor is operative to prevent access to said memory by said RAHI upon an assessment, by said first processor of a non-match of inputted VIF information pertaining to the PGHI with the stored VIF information pertaining to the RGHI.

27. The apparatus defined in claim 1, wherein:
  (a) said VIF is a pattern of an iris of an eye of the PGHI;
  (b) said computer memory is further operative to store a plurality of images of an iris of an eye of said RGHI, each image captured under different lighting conditions for said iris; and
  (c) said second SID is a light source configured to generate light which impinges on said PGHI iris thereby to alter an opening size of said PGHI iris, in response to said second supplementing signal;
  wherein said first processor is further operative to change said lighting conditions by generating said second supplementing signal;
  wherein said first processor is further operative to compare a plurality of captured images of said PGHI iris, each under different lighting conditions, with a plurality of stored RGHI iris images.

28. The apparatus defined in claim 1, wherein said second SID comprises a PGHI display device coupled to said first processor, located in proximity to said PGHI for displaying a representation of said second supplementing signal received from said first processor.

29. The apparatus defined in claim 28, wherein the information represented by said second supplementing signal causes said PGHI display device to produce a second prompt arranged to induce an alteration in at least one of:
  (a) the quantity of light impinging on an eye of said PGHI;
  (b) the focus of an eye of said PGHI;
  (c) a direction of gaze of an eye of said PGHI; and
  (d) an angle of orientation of a face of said PGHI with respect to said second camera.

30. The apparatus defined in claim 28, wherein:
  (a) said first processor is further operative to generate a first representation of a second information set, and to cause:
    (i) said first representation of said second information set to be stored in said computer memory, and
    (ii) said second supplementing signal to specify said first representation of said second information set;
  (b) in response to receipt of said second supplementing signal, said PGHI display device is adapted to produce a visual second representation of said second information set; and
  (c) said second camera is arranged to image both
    (1) said visible identifying feature of said PGHI, and
    (2) said PGHI display device displaying said visual second representation of said second information set,
  for generating a composite PGHI image containing both said identifying feature of said PGHI and said visual second representation of said second information set, for transmission to said first processor;
  wherein said first processor is further operative to:
    (i) receive said composite PGHI image and generate both
      (A) a third representation of said second information set, and
      (B) a representation of said VIF of said PGHI,
    each from the received composite PGHI image;
    (ii) compare information contained in said stored first representation of said second information set with information contained in said received third representation of said second information set;
    (iii) compare information contained in said stored RGHI VIF with information contained in said representation of said VIF of said PGHI; and
    (iv) prevent access of said PAHI to said memory if said first processor does not determine that both
      (A) said second information set comparison, and
      (B) said PGHI VIF comparison with said stored RGHI images,
    indicate respective substantially similar information matches;
  thereby to prevent PAHI access to said memory if said PGHI is not determined to be an RGHI.

31. The apparatus defined in claim 1, wherein said first processor is operative to allow deletion of said secure information in said memory by said PAHI in response to receipt of a third command signal and wherein said input device is further operative to provide said third command signal in response to a respective PGHI input.

32. The apparatus defined in claim 1, wherein said first processor is operative to allow alteration of said secure information in said memory by said PAHI in response to receipt of a fourth command signal and wherein said input device is further operative to provide said fourth command signal in response to a respective PGHI input.

33. The apparatus defined in claim 1, wherein said computer memory is further operative to store alphanumeric information related to at least one of:
said at least one RAHI, and
said at least one RGHI.

34. A method of controlling the access of a human individual to secure information in a computer memory comprising the steps of:
(a) storing, in a computer memory, each of
secure information;
information representing a plurality of images of a visible identifying feature ("VIF") pertaining to at least one registered accessing human individual ("RAHI") authorized to access said secure information; and
information representing a plurality of images of a VIF pertaining to at least one registered gatekeeping human individual ("RGHI") authorized to grant access to said secure information;
(b) receiving, by a processor, a request to identify a putative authorized human individual ("PAHI") as a RAHI;
c) based on receiving the request, generating, by the processor, at least one first VIF modifying signal and providing said signal to a first VIF modifying device;
d) receiving, by the first VIF modifying device, the first VIF modifying signal;
e) in response to the received first VIF modifying signal, producing, by the first VIF modifying device, an output, and providing the output in the vicinity of the PAHI, wherein the output induces a change in an appearance of the VIF of the PAHI;
f) repeatedly capturing, by a first digital camera, a plurality of images of the VIF of the PAHI following the providing of the output, and providing information representing the PAHI VIF images to the processor;
g) repeatedly comparing, by the processor, (1) the information representing the images of the VIF of the PAHI with (2) the stored information representing the VIF of the RAHI, and determining a match between the stored VIF information of the RAHI and the inputted VIF information of the PAHI;
h) generating, by the processor, at least one assessment signal representing a result of said comparing;
i) displaying, by a display device, a representation of said assessment signal;
j) generating, by the processor, at least one second VIF modifying signal and providing said signal to a second VIF modifying device;
k) receiving, by the second VIF modifying device, the second VIF modifying signal;
l) in response to the received second VIF modifying signal, producing, by the second VIF modifying device, a supplemental output, and providing the supplemental output in the vicinity of a putative gatekeeping human individual ("PGHI"), wherein the supplemental output induces a change in an appearance of a VIF of the PGHI;
(m) capturing, by a second digital camera, a plurality of images of the VIF of the PGHI including at least one image following the providing of the supplemental output, and providing information representing the PGHI VIF images to the processor;
(n) comparing, by the processor, (1) the information representing the images of the VIF of the PGHI with (2) the stored information representing the VIF of the RGHI, and determining a match between the stored RGHI VIF information and the inputted PGHI VIF information; and
(o) inputting, by an RGHI input device, a grant access command, and, upon a determination of a match between said PGHI VIF information and said RGHI VIF information, permitting access by a PAHI to the secure information.

* * * * *